(12) United States Patent
Gressick et al.

(10) Patent No.: US 11,583,604 B1
(45) Date of Patent: Feb. 21, 2023

(54) ODOR EMISSION SYSTEM, DEVICE AND METHOD

(71) Applicant: Barron Associates, Inc., Charlottesville, VA (US)

(72) Inventors: William T. Gressick, Charlottesville, VA (US); Brian R. Clark, Charlottesville, VA (US); Clifford Schultz, Perkins, OK (US)

(73) Assignee: Barron Associates, Inc., Charlottesville, VA (US)

( * ) Notice: Subject to any disclaimer, the term of this patent is extended or adjusted under 35 U.S.C. 154(b) by 170 days.

(21) Appl. No.: 16/861,455

(22) Filed: Apr. 29, 2020

(51) Int. Cl.
| | | |
|---|---|---|
| *A61L 9/03* | (2006.01) | |
| *A01K 15/02* | (2006.01) | |
| *A01K 5/02* | (2006.01) | |
| *F17C 13/04* | (2006.01) | |

(52) U.S. Cl.
CPC ............ *A61L 9/035* (2013.01); *A01K 5/0275* (2013.01); *A01K 15/02* (2013.01); *A61L 9/032* (2013.01); *F17C 13/04* (2013.01); *A61L 2209/11* (2013.01); *A61L 2209/134* (2013.01)

(58) Field of Classification Search
CPC ...... A61L 9/035; A61L 9/032; A61L 2209/11; A61L 2209/134; A01K 5/0275; A01K 15/02; F17C 13/04
See application file for complete search history.

(56) References Cited

U.S. PATENT DOCUMENTS

| | | | |
|---|---|---|---|
| 4,603,030 A | 7/1986 | McCarthy | |
| 5,767,385 A | 6/1998 | Bundy et al. | |
| 7,011,795 B2 | 3/2006 | Thompson et al. | |
| 8,821,802 B2 | 9/2014 | Haran | |
| 2006/0039835 A1 | 2/2006 | Nottingham et al. | |
| 2006/0251541 A1 | 11/2006 | Santandrea | |
| 2010/0059602 A1* | 3/2010 | Chiou | A01M 1/2038 239/70 |
| 2015/0083755 A1* | 3/2015 | Meeker | F16M 13/02 222/183 |
| 2017/0064924 A1 | 3/2017 | Stout | |
| 2018/0110457 A1* | 4/2018 | Smith | A61B 5/4011 |
| 2019/0388576 A1* | 12/2019 | Medina Rivero | A61L 9/127 |

FOREIGN PATENT DOCUMENTS

| | | |
|---|---|---|
| WO | 2010058380 | 5/2010 |
| WO | 2016164917 | 10/2016 |

OTHER PUBLICATIONS

Wikipedia, "Butterfly Valves" (Year: 2018).*
Wikipedia, "Rotary Valve" (Year: 2018).*

* cited by examiner

*Primary Examiner* — Sean E Conley
*Assistant Examiner* — Brendan A Hensel
(74) *Attorney, Agent, or Firm* — Williams Mullen; Thomas F. Bergert

(57) ABSTRACT

Embodiments of a controlled odor emission system and device include an odor presentation port tube and an odor tray securely retained against a platform, a valve housing securable to the platform adjacent the tray, a valve secured within the valve housing and an actuator for moving the valve. By controlling movement of the valve, precise amounts of an odor can be dispensed under programmatic control for training animals. Further, a system incorporating a central control unit and a reward dispenser in communication with an odor emission device to facilitate animal training.

12 Claims, 14 Drawing Sheets

ODOR EMISSION SYSTEM, DEVICE AND METHOD

STATEMENT

This invention was made with U.S. Government support under contract no. W911NF-16-C-0104 awarded by the United States Army. The Government has certain rights in the invention.

TECHNICAL FIELD

The present disclosure pertains to behavioral olfactory conditioning and, more specifically, to a controllable odor emission system, device and method for effectively emitting odors.

BACKGROUND AND SUMMARY

Many law enforcement and military operations benefit from the detection of odors that may be indicative of unscrupulous activities or targeted substances. Oftentimes, animals such as rats or dogs are trained for such odor detection purposes. Separately, cosmetics and food developers can employ odor detection systems and devices to facilitate odor signature development for various products.

Unfortunately, current odor-emitting devices and systems used for training are not controllable or automated, require significant human attention, do not always dispense precise amounts of odor(s), blend odors in an unintended way, cannot predictably repeat desired odors, may cross-contaminate odors and/or may leak in ways that compromise training. Further, present devices and systems are generally not portable or suitable for field use. Additionally, present devices and systems do not have an effective means of cleaning or purging odors that may adhere to surfaces over repeated use.

Embodiments of the present disclosure provide a computer-controlled system including one or more portable modular devices that dispense precise amounts of odor(s) and/or rewards under programmatic control to imprint desired behaviors such as search and marking of desired compounds on animals. The present disclosure also facilitates the collection and analysis of extensive data that permits monitoring of animal performance and comparison across animals.

Embodiments of the device as described herein minimize leakage of odors, which is of particular importance with explosive materials that are designed to be detected in very low concentrations. Embodiments of the present device also provide known and highly repeatable odor concentrations at known levels for consistent scientific validation studies and training in animals. Further, embodiments of the present device allow mixing of multiple odors at various concentrations to test animals' abilities to discriminate odors amid a stronger background scent. The device is versatile and can be adapted in size to suit different animal trainees. Programming associated with the present disclosure assists in acquiring animal behavioral information and performing detailed analyses and comparisons between animals and over time. In various embodiments, algorithms are employed to predict animal success at later stages given data only from early training.

In various embodiments, the system as described herein can train small animals to locate and detect explosive odors through behavioral conditioning. Devices as disclosed herein present odor as the only unique cue presented to the animal. In various embodiments, the devices have identical audible and visual appearance whether they are emitting target odor, distractant odor, or control odor. The system is highly modular and reconfigurable to suit a variety of training scenarios and objectives.

DETAILED DESCRIPTION

Figure 1:
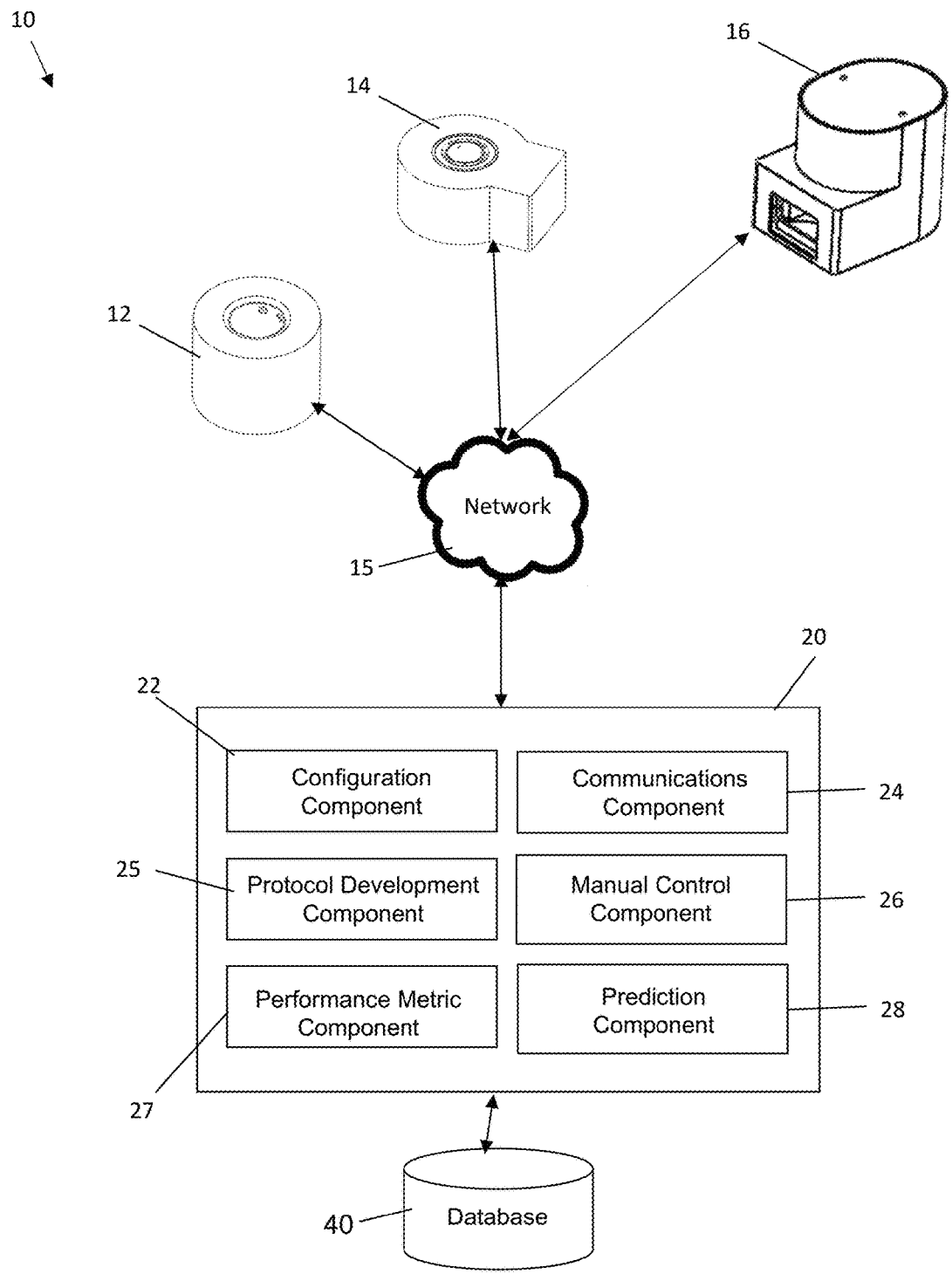
FIG. 1 is a schematic diagram of a system incorporating an odor emitting device in accordance with embodiments of the present disclosure.

The presently disclosed subject matter now will be described more fully hereinafter with reference to the accompanying drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims.

It will be appreciated that reference to "a", "an" or other indefinite article in the present disclosure encompasses one or more than one of the described element. Thus, for example, reference to a processor may encompass one or more processors, a canister may encompass one or more canisters, a tray may encompass one or more trays and so forth.

As shown in FIGS. 1 through 4, in various embodiments, the system 10 includes portable odor-emitting canisters or devices (e.g., 12, 14) that emit a target odor (e.g., TNT or other explosives, or other controlled substances) as directed by a base station or central control unit 20, as well a portable reward dispenser 16 that provide rewards to the animals upon successful completion of the behavioral tasks. These devices can be battery powered, can communicate via wireless links, can be modular, reconfigurable and scalable, and can be used as part of training enclosures/chambers, in open room environments, and in outdoor settings. In the case of rats, the reward dispenser provides a solid sucrose or protein pellet as reinforcement, but the system is adaptable to a variety of other reward types such as a tennis ball launcher for canines, for example, if desired. In various embodiments, the wireless communication capability of the reward system can be integrated into a specially designed device or supplied as an auxiliary add on to allow an otherwise unmodified existing reward device to function in communication with the central control unit 20 as discussed elsewhere herein. The devices are robust to animal damage. Any number or combination of devices can be used and the system can automatically configure itself to the available devices. In various embodiments, a graphical user interface associated with a software application provides an interface for the end-user to the system. The software computes and stores performance metrics in a database for analysis and performance comparisons. A scripting environment is provided to allow development of automated training protocols. It will be appreciated that device functions can be controlled by the central control unit 20 either manually or through the automated scripting environment.

The system 10 can include a central control unit 20 comprising a laptop, tablet, smartphone or similar device running system software, wherein the device can act in part as a base station, or can connect in wired or wireless fashion to a base station, wherein the base station houses one or more radio transceivers to communicate with remote devices 12, 14 and/or 16. The radio transceiver(s) act as a communications component 24 as shown in FIG. 1. In various embodiments, the system 10 supports any number of remote devices, which are broadly categorized into odor-emitting devices 12, 14 and reward dispensers 16. Sub-categories of each device type are described below. Each device identifies itself upon power-up and the base station (e.g., 28) and the system software perform the necessary configuration to allow proper function of the devices. In various embodiments, the control unit 20 includes a configuration component 22 to manage device configurations.

In embodiments in which the central control unit 20 communicates with a device such as devices 12, 14 and/or 16 through a data network 15, the data network 15 can be a local area network (LAN), a wide area network (WAN), a public network such as the Internet, or a private network. The devices 12, 14, 16 and the central control unit 20 are configured to connect to the data network or remote communications link in any suitable manner. In various embodiments, such a connection is accomplished via: a conventional phone line or other data transmission line, a digital subscriber line (DSL), a T-1 line, a coaxial cable, a fiber optic cable, a wireless or wired routing device, a mobile communications network connection (such as a cellular network or mobile Internet network), or any other suitable medium.

In various embodiments, odor-emitting device 12 is a two-odor device whereas odor-emitting device 14 is a four-odor device, although many other embodiments with different numbers of odor-emitting devices can be provided according to the present disclosure. Odor-emitting device 12 can be considered a more compact device than device 14. Regardless of embodiment, each type of device or canister 12, 14 includes one or more valves that alternatively seals or allows the contents of an odor compartment to permeate into the atmosphere under natural diffusion or fan-forced convection where animals detect it. It will be appreciated that embodiments of the device disclosed herein assist where either a target odor, a distractant odor, a mixed target-distractant odor or a control odor are mutually exclusively presented to the animal trainee. Each valve can include a valve cylinder which can be constructed of ceramic-coated aluminum, for example, which minimizes absorption of odor molecules. The rounded surface of the valve cylinder can rotate within a valve sleeve or bushing, for example, which is fit to a tight tolerance to minimize leakage. In various embodiments, the valve sleeve or bushing is formed of brass or stainless steel material. An electromechanical actuator can rotate the valve cylinder within the sleeve to allow the contents of an odor chamber to mix with the atmosphere through ports in the sleeve. Because the tolerance between the valve cylinder and valve sleeve is so tight, any debris that enters the valve from the odor tube (which is exposed to the animal) is simply "pushed" along the edge of the valve as it closes and enters the odor compartment where it is periodically removed during cleaning.

As shown in FIG. 1, the central control unit 20 can be provided with various components that can be configured as software, firmware, hardware or a combination thereof. Configuration component 22 permits devices such as 12, 14 and/or 16 to be configured for operation with and by the central control unit 20. Communications component 24 provides programming permitting communications between central control unit 20 and devices 12, 14, 16. Protocol development component 25 provides programming enabling a user to establish protocols for operation of the devices 12, 14 and/or 16. For example, an end user may develop a protocol using component 25 that selectively opens and closes ports in an odor-emitting device such as 12 or 14 to train a specific type of animal, such as a rat or canine, for example. The protocol may be developed to adjust factors such as the timing of exposure, the amount of rotation of a valve within the device, the flushing out of a device, amount of heat from a heater element 98 secured to the device 12, 14 and other factors. The manual control component 26 includes programming for permitting a user to manually control a device such as 12, 14 or 16. The performance metric component 27 can include programming for obtaining and analyzing operational data from the use of the control unit 20 with devices 12, 14 and/or 16. Prediction component 28 provides programming for predicting animal success at later stages given data only from early training. Various data associated with the use and operation of the system 10, whether structured or unstructured, can be stored in database 40 and is accessible to the various components of the central control unit 20.

As shown in FIGS. 2 through 16, odor-emitting device 14 includes internal components 50 secured to or maintained around a platform 52. For example, a tube receiver 54 securely retains an odor presentation port tube 58 above the platform 52, and the tube receiver 54 includes a rim 55 forming a rim opening 56 therein. The odor presentation port tube 58 is positioned within the rim opening 56 of the tube receiver 54 and extends downwardly through the opening 56 to be securely retained against the top surface 53 of the platform 52. The opening 56 becomes an odor channel for odors to be emitted in accordance with the operation of the device as described herein. The odor presentation port tube 58 can be formed with one or more wall openings 62, 63 therein. In various embodiments, neither the tube receiver 54 nor the odor presentation port tube 58 is directly secured to the platform 52, but are held in position by secure connections (e.g., machine screws) that connect the top surface 53 of the platform 52 to one or more valve housings 70 and further connect the one or more valve housings 70 to arms 59 on the tube receiver 54. The odor presentation port tube 58 and tube receiver 54 can be removed for cleaning as necessary. In various other embodiments, no odor presentation port tube is provided and the tube receiver facilitates operation as described herein with respect to the odor presentation port tube.

Figure 3:
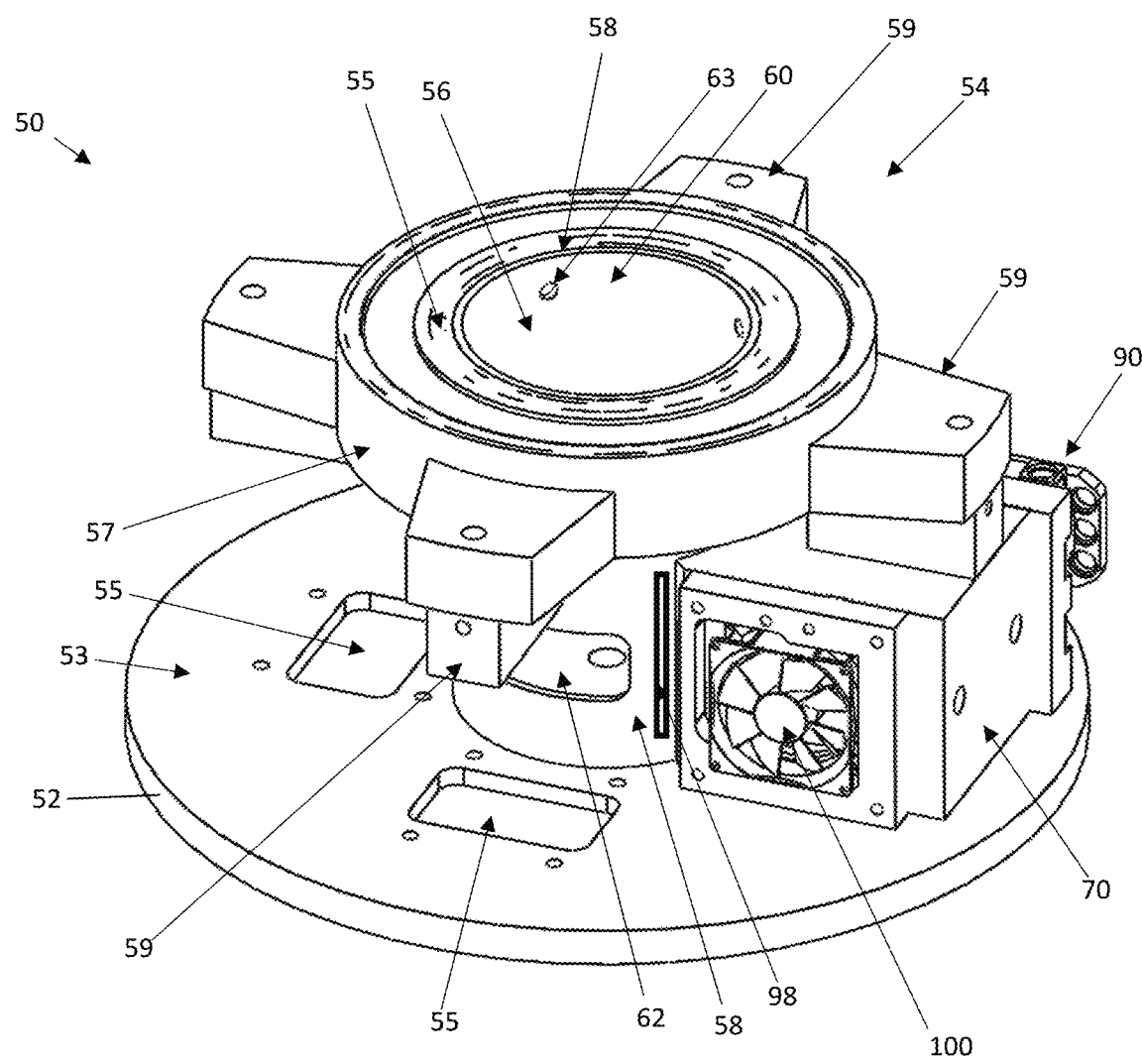
FIG. 3 is a perspective view of components of an odor emitting device in accordance with embodiments of the present disclosure.
Figure 4:
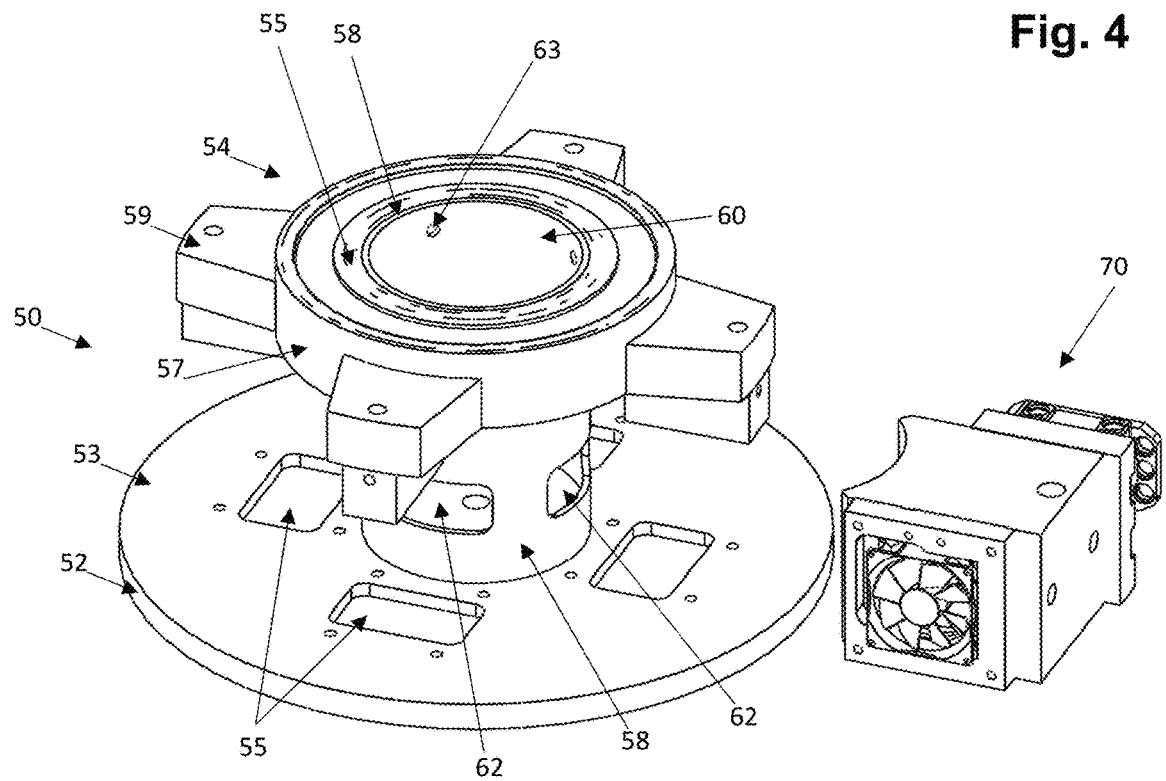
FIG. 4 is a top right perspective view of components of an odor emitting device with a detached valve in accordance with embodiments of the present disclosure.

One or more trays 64 are removably securable to a tray base 65. In various embodiments, the tray base 65 is provided with indentations or openings 67 for receiving the trays 64. The tray base 65 may further have connector elements (e.g., 68) which can be used to secure the tray base 65 to the bottom side 51 of the platform 52 of the odor-emitting device 14. Connector elements 68 can be openings for permitting a screw or bolt to pass therethrough and mate with a receiving element such as a thread on the bottom side 51 of the platform 52, for example. The platform can further be formed with orifices 55 which align with respective openings 67 in the tray base 65 to permit fluid flow as described elsewhere herein. The tube receiver 54 can also be provided with arms 59 extending radially outwardly of a base portion 57 of the tube receiver 54, wherein each arm 59 is securable to a respective valve housing 70 to assist in holding the valve housing 70 in place, as shown in FIG. 3.

In various embodiments, a head detector (not shown) is aligned with openings 63 in the side wall 60 of the odor presentation port tube 58. The head detector or head poke sensor can be provided as opposed phototransistor/LED pairs secured to the tube receiver and aligned with openings 63 on either side of the odor presentation port tube 58, for example, wherein the opposed phototransistor pairs act to detect the head of the animal and report the detection to the microcontroller 120 which, in various embodiments, reports to the central control unit 20 so as to trigger a reward. In the embodiment where no odor presentation port tube is provided, no head poke detector or head poke sensor would be provided.

In various embodiments, each valve housing 70 is securable such as by screws or the like to a respective arm 59 of the tube receiver 54 and also to the platform 52 adjacent to or above each tray 64. A valve 72 is secured within each valve housing 70. As shown in FIGS. 2 through 8, for example, the valve 72 can include a valve cylinder 74 and a valve sleeve 76 operably connected to permit openings 77, 78 formed in the side wall 75 of the sleeve 76 to adjustably align with a fluid opening or fluid slot 79 in the side wall 73 of the cylinder 74 as the valve cylinder 74 is rotated during operation. In various embodiments, the valve cylinder 74 includes a bottom floor 80 at a first end 81 and a top rim 82 at a second end 83, wherein the rim 82 defines an opening 85 for permitting air to flow from a fan 100 as described elsewhere herein. The bottom floor 80 can be provided with connector elements (not shown) on the axially outer side of first end 81 for securely connecting to head 92 of an actuator 90. This connection permits the valve cylinder 74 to be rotated by the actuator 90 during operation. In various embodiments, the actuator 90 is secured to a block 94 that is secured to the valve housing 70. The valve sleeve 76 also has an upper rim 95 that defines an upper opening 96 that permits air to flow from a fan 100 as described elsewhere herein. The fan 100 can be secured to a fan frame 102 that is secured to the valve housing 70 such as by machine screws or the like. In various embodiments, the fan 100 is secured to the valve housing 70 at a first end 104 of the valve housing 70 and the actuator 90 is secured at a second end 106 of the valve housing 70 that is opposite the first end 104. The fan 100 can be provided as a variable speed/flow rate fan in accordance with embodiments of the present disclosure. The valve housing 70 is formed with slots 110, 112 to permit fluid flow from the trays 64 through the valve 72 and the odor presentation tube wall openings 62, depending upon the desired operation of the device 14. As shown in FIGS. 5 through 8, slot 110 is aligned with platform opening 55 and tray base opening 67 for a given tray 64 and slot 112 (not shown in FIG. 5) is aligned with opening 62 in odor presentation port tube 58.

Figure 2:
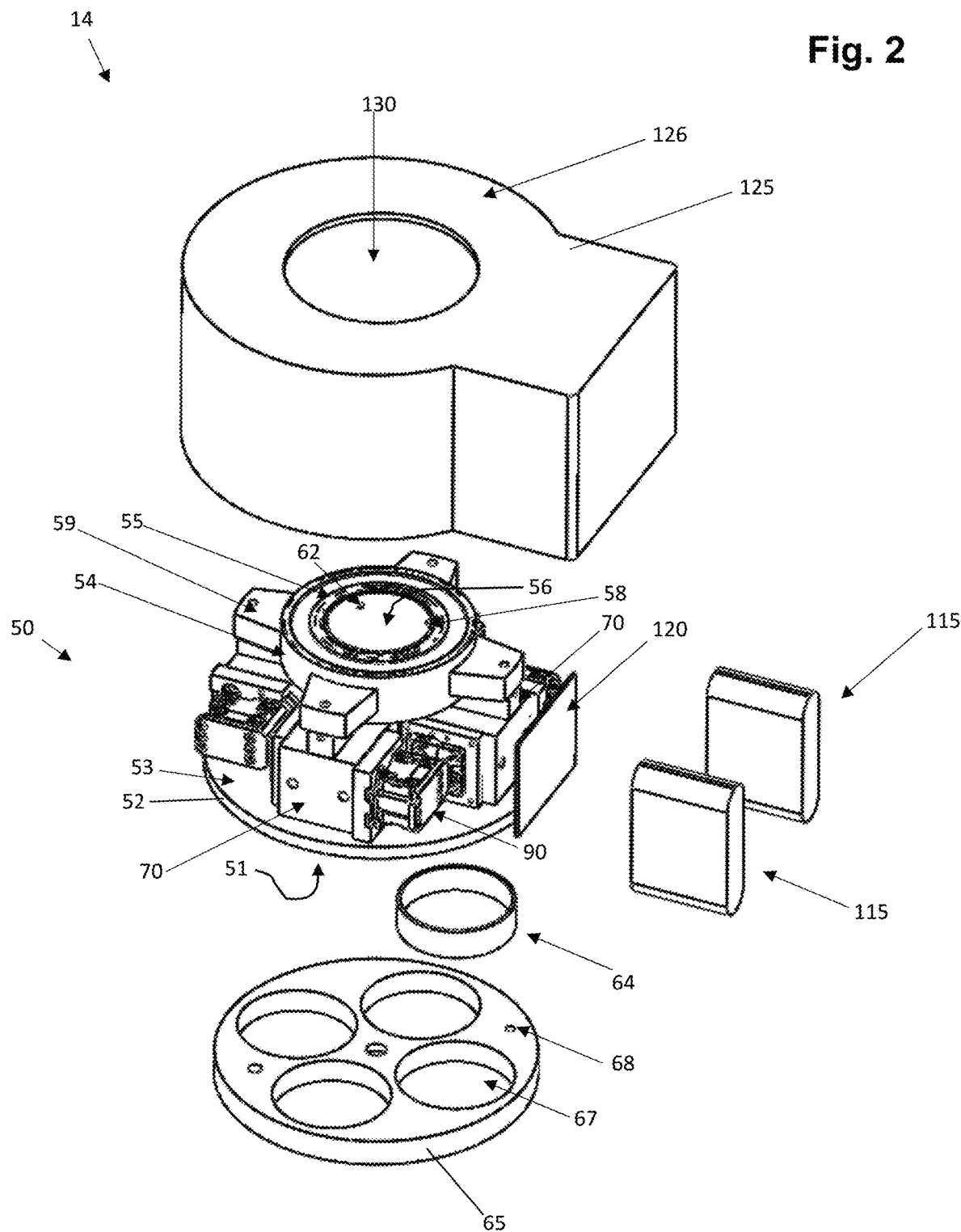
FIG. 2 is an exploded perspective view of an odor emitting device in accordance with embodiments of the present disclosure.

The actuator 90 and the fan 100 can be operable using at least one battery 115 and at least one controller 120 secured to the device 14. The battery 115 can be a nickel-metal hydride or lithium-ion battery, for example. The actuator 90 operates the valve cylinder 74 to permit desired operation. A cover 125 can also be provided for housing and/or covering the interior components 50 of the device 14, wherein the cover 125 can be formed with an opening 130 at the top end 126 to permit fluid flow as desired in accordance with the present disclosure. As shown in FIG. 2, the cover 125 can be positioned around the tube receiver 54, the platform 52 and the tray base 65 containing the trays 64. The cover 125 can be considered a housing defining an odor channel 130 in various embodiments, wherein the cover 125 houses the odor tray(s) 64, the controller 120, actuator 90, head detector and valve(s) 72.

As shown in FIGS. 8 through 16, the valve cylinder 74 and the valve sleeve 76 cooperate to form a substantially cylindrical valve 72 defining adjustable odor openings 77, 78. The actuator 90 is adapted to rotate the valve cylinder 74 under control of the controller 120 so as to position the odor opening 77 between a full fluid communication position with the underlying tray 64 and a blocked fluid communication position with the underlying tray 64.

In operation of device 14, the trays 64 can be set up to contain different odor source materials as desired for operational training. In various embodiments, a first tray houses a target odor source material, the second tray houses a control odor source material, the third tray houses a distractor odor source material and the fourth tray houses a second target odor source material. The controller 120 receives instructions from central control unit 20 regarding a desired odor flow, such as may be established via protocol development component 25, and the fan 100 and/or actuator 90 are operated accordingly. For example, the fan 100 can force air across the odor sample in the odor chamber, when desired. Thus, for the device 14 shown in FIGS. 2 through 16, four valves are provided and individually secured to a respective actuator, wherein each of the actuators is adapted to rotate a respective one of the four valves, such that odors associated with the odor source materials can be selectively mixed.

Figure 9:
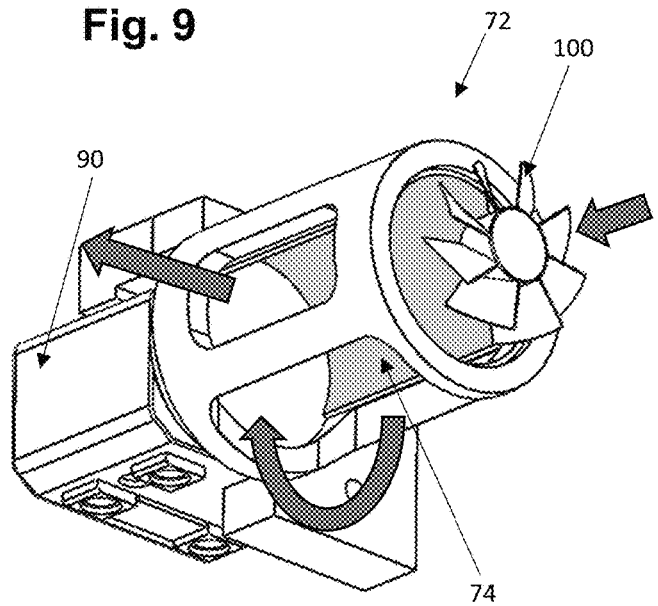
FIG. 9 is a perspective view illustrating valve operation of a valve in the fully open position.
Figure 10:
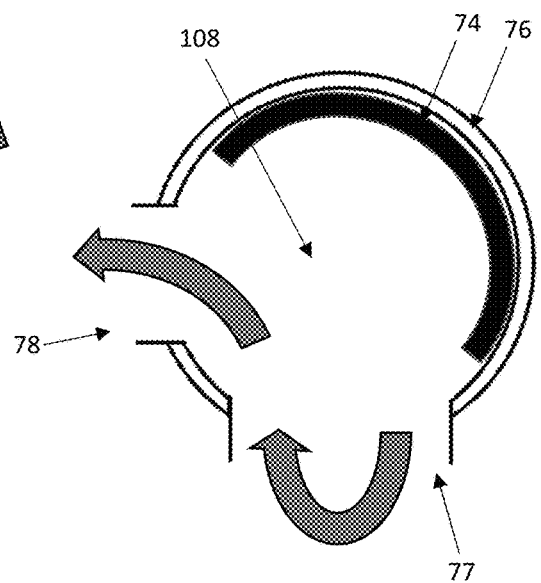
FIG. 10 is a schematic diagram illustrating valve operation of a valve in the fully open position.

FIGS. 9 and 10 illustrate the valve 72 in the fully open position. As indicated by the arrows, the fan 100 draws air into the odor chamber 108 and, with valve sleeve opening 77 exposed due to the position of the valve cylinder 74, the contents of the odor source material in the underlying tray are swept over by incoming air, bringing the odor through the opening 55 in the platform 52 (see FIG. 4). The odor then follows the fluid pathway out of the opening 78 in the valve sleeve 76, whereby it travels through opening 62 in odor presentation port tube 58 and up the opening 56 into the ambient environment (see FIG. 4). Upon an animal sensing the odor and positioning its head, nose or other body part into the tube 58, it can be sensed by the head detector through an opening 63 so as to trigger a reward by the reward dispensing device 16. The valve cylinder 74 is rotated to the fully open position by the actuator 90, which is controlled by the embedded microcontroller 120 and remote central control unit 20. It will be appreciated that air can also flow via natural convection without the assistance of a fan. The central control unit 20 can thus initiate valve operation on the device 14 by sending a communication to the microcontroller 120 which directs the operation of the actuator 90 and/or fan 100. When the head detector senses animal movement, the head detector signals the microcontroller 120 which conveys a return communication to the central control unit 20. The central control unit 20 then conveys a message to the reward dispenser 16 to dispense a reward based on the animal's reaction to the odor detection.

Figure 11:
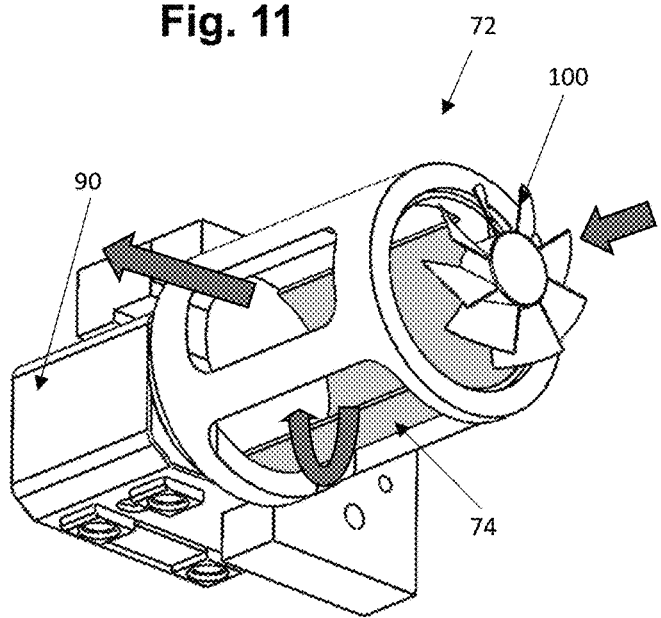
FIG. 11 is a perspective view illustrating valve operation of a valve in the partially open position.
Figure 12:
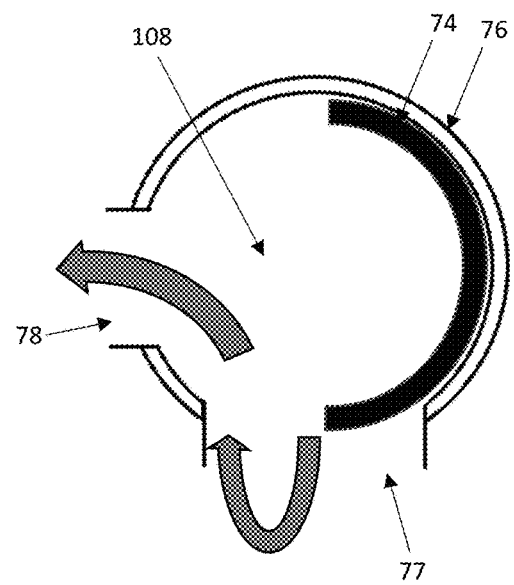
FIG. 12 is a schematic diagram illustrating valve operation of a valve in the partially open position.

FIGS. 11 and 12 illustrate a valve 72 in the partially open position. Should a smaller amount of odor be desired, perhaps to test the sensitivity of a particular animal to a particular odor, for example, the actuator 90 can rotate the valve cylinder 74 so as to partially occlude the lower valve sleeve opening 77 and reduce the amount of odor source material exposed to the airflow. The fan 100 can be operated as described earlier, causing the material in the odor source material in the underlying tray 64 to be swept over to a lesser degree by incoming air, bringing the odor through the opening 55 in the platform 52 (see FIGS. 2 and 4). The odor then follows the fluid pathway out of the opening 78 in the valve sleeve 76, whereby it travels through opening 62 in odor presentation port tube 58, through odor channel 56 and into the ambient environment. Should an animal detect the odor, the system operates as described in connection with FIGS. 9 and 10 above.

Figure 13:
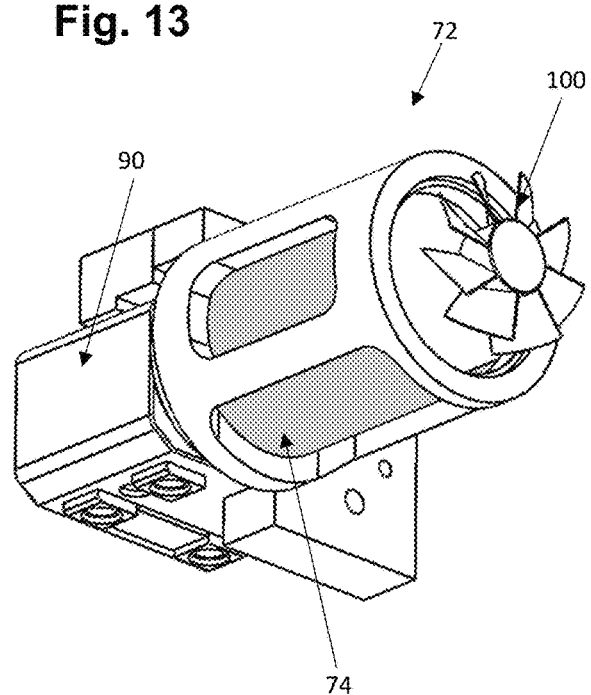
FIG. 13 is a perspective view illustrating valve operation of a valve in the fully closed position.
Figure 14:
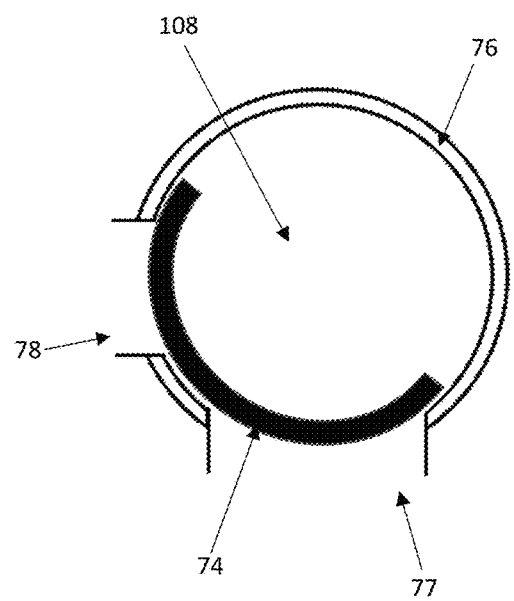
FIG. 14 is a schematic diagram illustrating valve operation of a valve in the fully closed position.

FIGS. 13 and 14 illustrate device operation when valve 72 is in the fully closed position. In this position, the fan 100 is not operated, and no odor is permitted into or out of the odor chamber 108, as the valve cylinder 74 has been rotated so as to close off the openings 77, 78 in the valve sleeve 76. This position can be employed when the odor from the odor source material in the underlying tray is not to be exposed to the atmosphere, perhaps when a different odor tray or combination of different odor trays are employed. Each valve can thus be closed when other odors are being presented to the animal, or the device is not being used at all.

Figure 5:
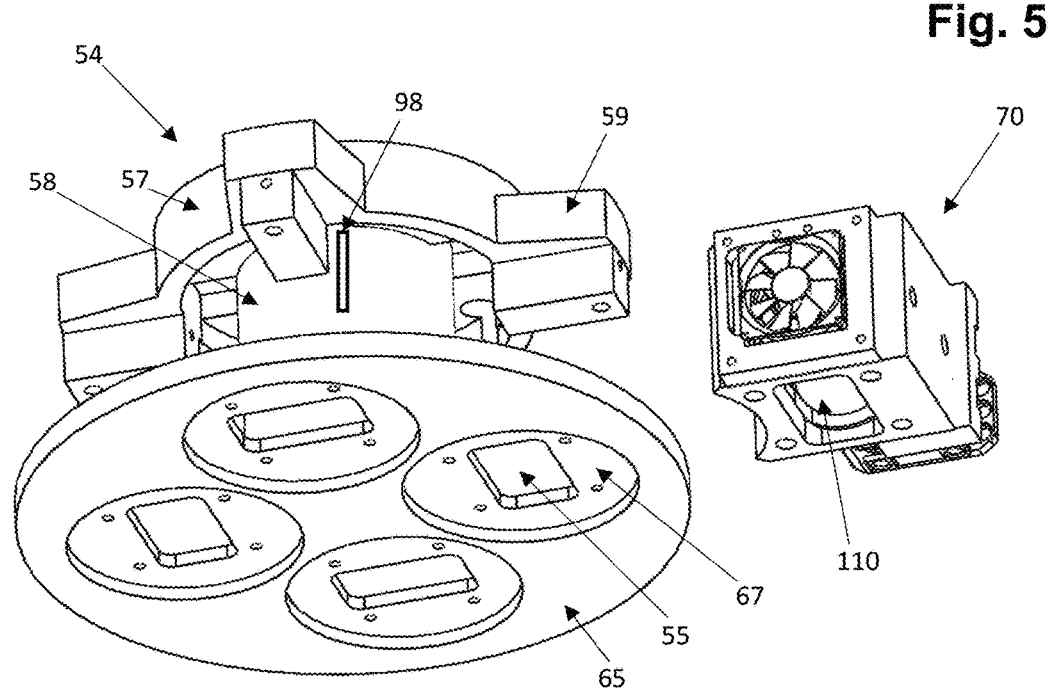
FIG. 5 is a bottom right perspective view of components of an odor emitting device with a detached valve in accordance with embodiments of the present disclosure.
Figure 6:
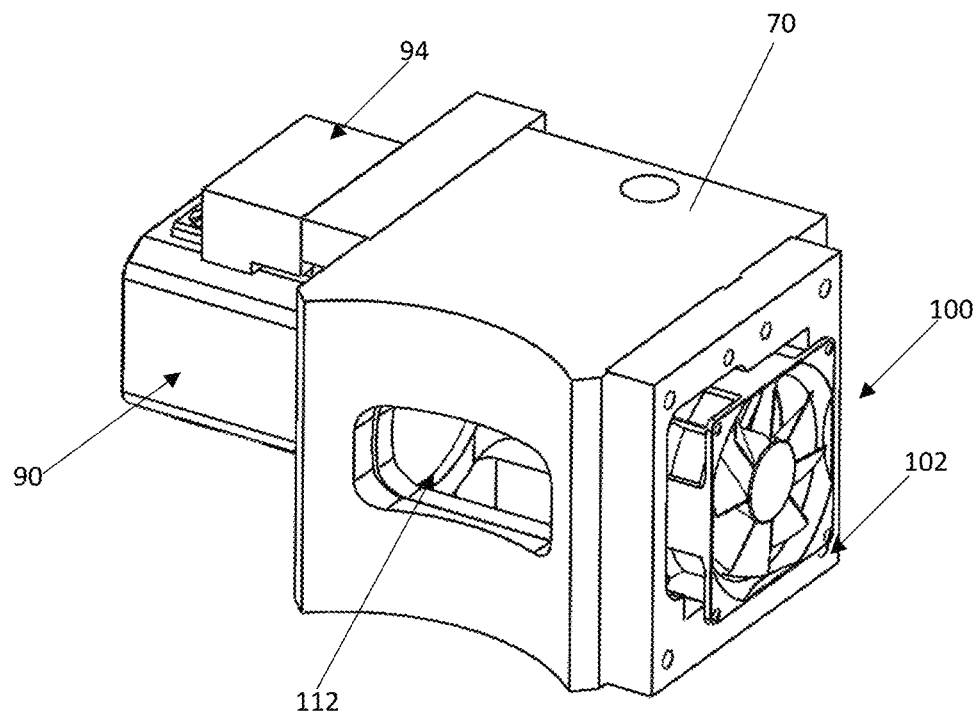
FIG. 6 is a front right perspective view of a valve housing in accordance with embodiments of the present disclosure.
Figure 7:
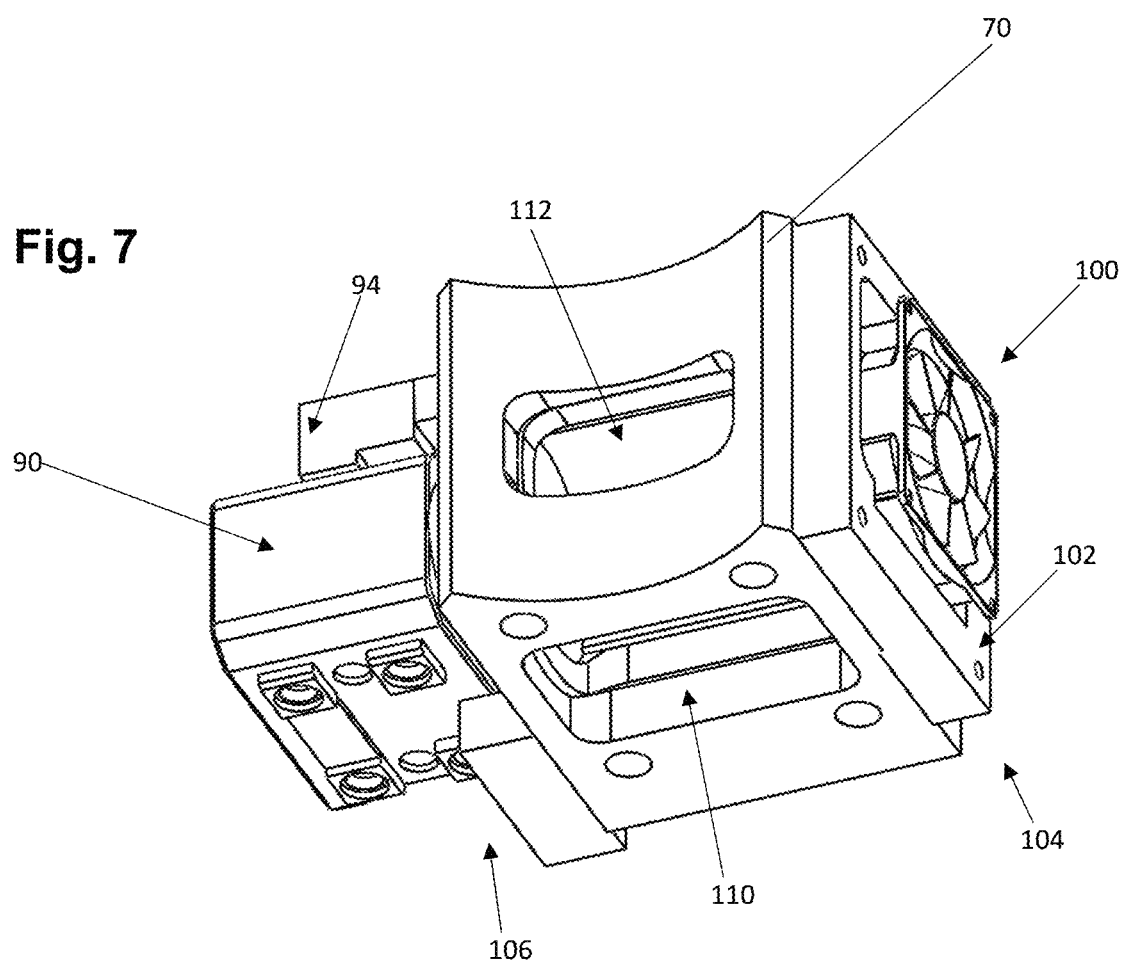
FIG. 7 is a bottom right perspective view of a valve housing in accordance with embodiments of the present disclosure.
Figure 8:
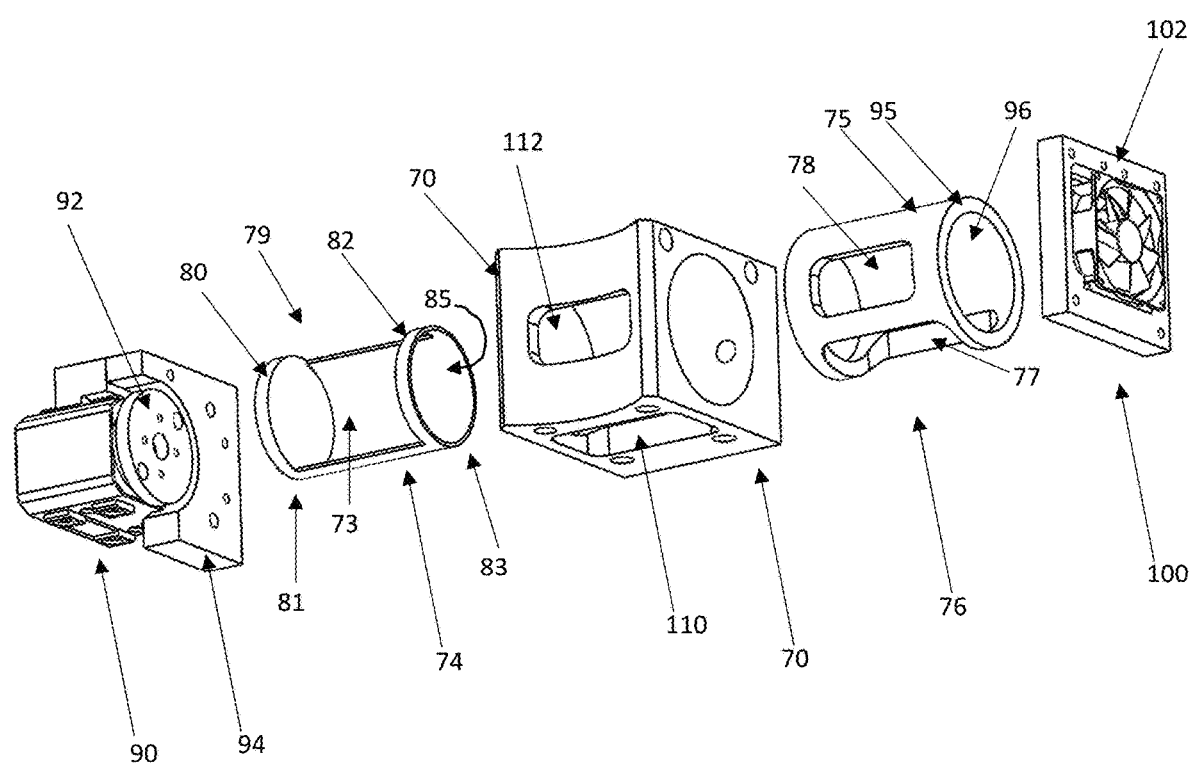
FIG. 8 is an exploded perspective view of a valve in accordance with embodiments of the present disclosure.
Figure 15:
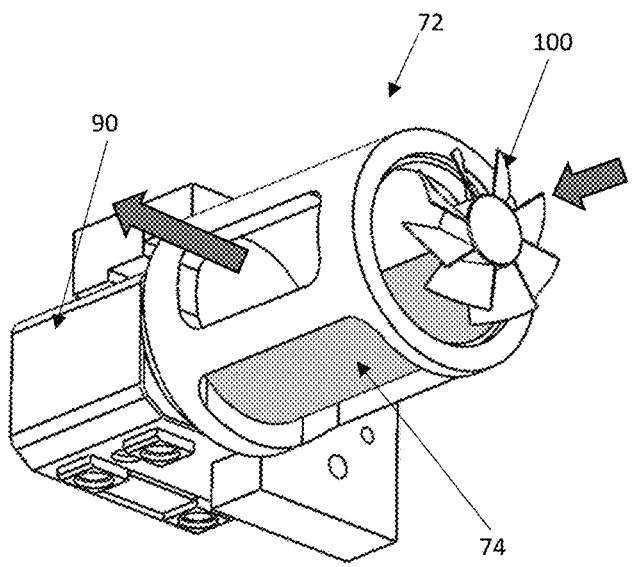
FIG. 15 is a perspective view illustrating valve operation of a valve in the flush open position.
Figure 16:
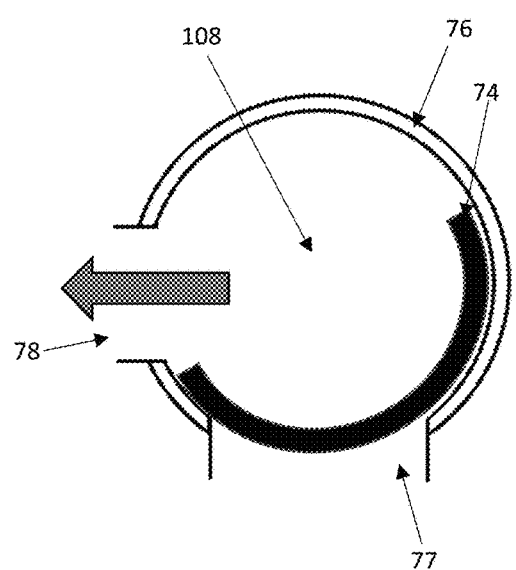
FIG. 16 is a schematic diagram illustrating valve operation of a valve in the flush open position.
Figure 17:
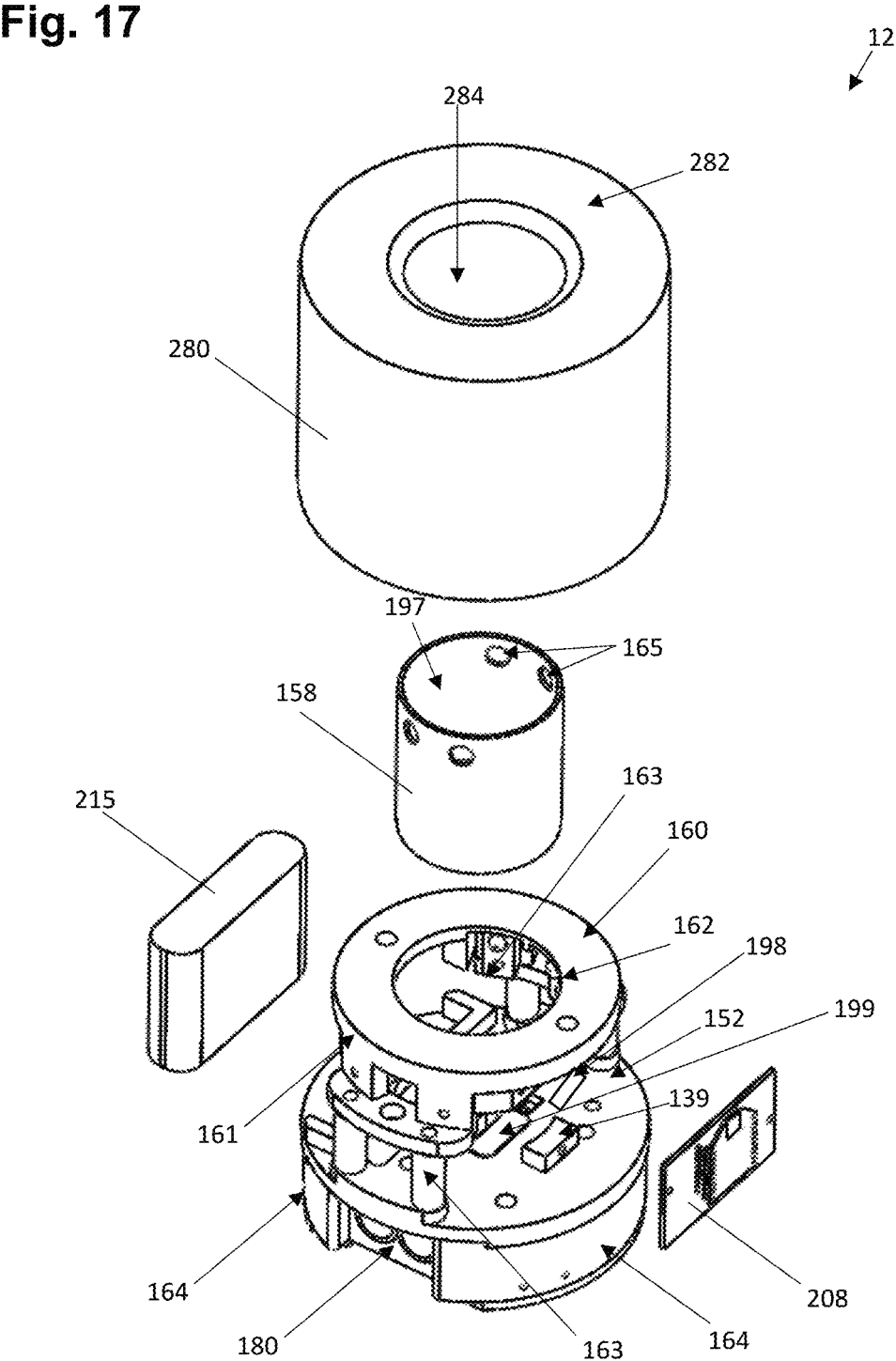
FIG. 17 is an exploded perspective view of an odor emitting device in accordance with additional embodiments of the present disclosure.
Figure 18:
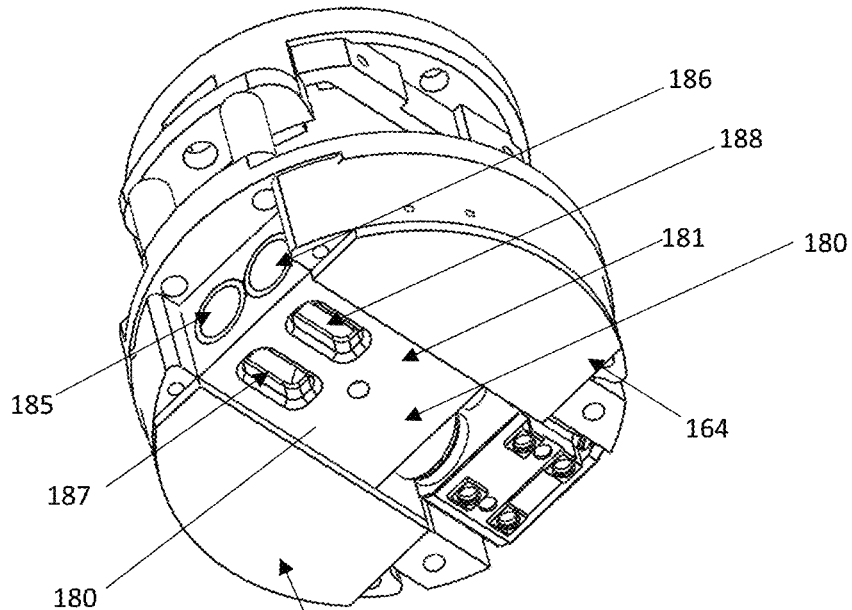
FIG. 18 is a bottom perspective view of components of the odor emitting device of FIG. 17.
Figure 19:
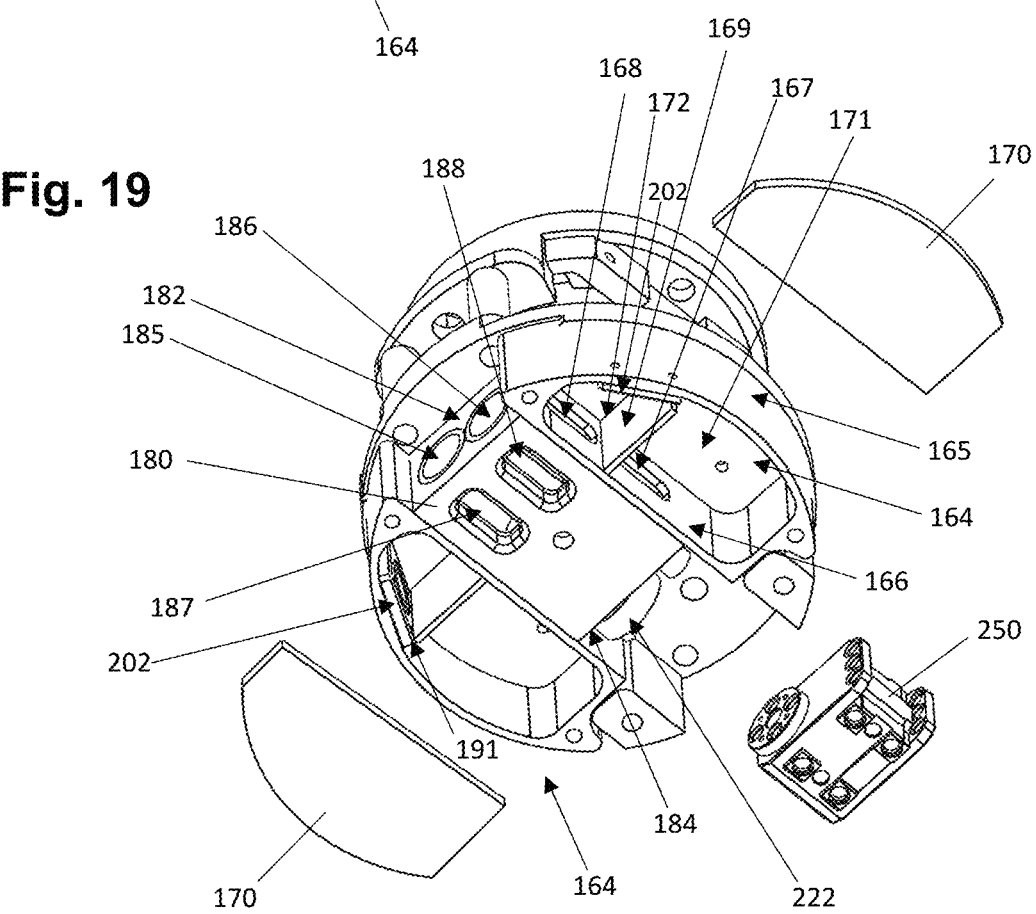
FIG. 19 is a bottom perspective view of components of the odor emitting device of FIG. 17 with covers and actuator detached.

FIGS. 15 and 16 illustrate device operation when valve 72 is in the flush open position. In this position, the fan 100 operates to blow fresh air and any retained odor out of the odor chamber 108 and through the opening 78 in the valve sleeve 76. The valve cylinder 74 closes off the lower opening 77 in the sleeve 76, such that any odor in an underlying tray is blocked from entering the odor chamber 108. In various embodiments, as shown in FIGS. 3 and 5, a resistive electric heating element 98 is in contact with or proximate the odor presentation port tube 58 and can be energized via controller 120 to heat the surface of the tube 58 to further promote the release of adsorbed odor molecules and/or surface contaminants.

As shown in FIGS. 17 through 26, alternative odor-emitting device 12 includes a pair of odor trays 164, a platform 152 and a tube receiver 160 secured above the platform 152, wherein the tube receiver 160 has an internal rim 162 forming an opening 163. In various embodiments, the tube receiver 160 is secured at its radially outer end(s) 161 to one or more support braces 163 which are secured atop the platform 152 using machine screws or the like. A substantially cylindrical odor presentation port tube 158 is positionable within the rim opening 163 of the tube receiver 160 and securely maintained atop the platform 152. For example, the odor presentation port tube 158 can be retained in position by one or more guides 139 secured atop the platform 152. The odor presentation port tube 158 is formed with one or more openings 165 therein, which can be aligned with one or more head detectors in or on the tube receiver, similar to the arrangement described elsewhere herein in connection with device 14. A removable cover 280 can be formed with an opening 284 at the top end 282 to permit fluid flow as desired in accordance with the present disclosure. The cover 280 can house and/or be positioned around the tube receiver 160, the platform 152 and the trays 164. The cover 280 can be considered a housing defining the odor channel 284 in various embodiments, wherein the cover 280 houses the odor tray(s) 164, the controller 208, actuator 250, head detector and valve(s) 191, 192.

One or more trays 164 are removably securable to the platform 152 such as by screws or the like. The trays 164 can be formed with walls 165, 166. In various embodiments, wall 165 is curved and wall 166 is substantially flat, wherein wall 166 is formed with first 167 and second 168 fluid slots. A baffle 169 can also be provided and may at least partially divide the fluid chamber enclosed by the walls 165, 166 into multiple chambers 171, 172. The baffle 169 does not necessarily extend all the way from wall 166 to wall 165, but a gap 191 may exist between the baffle 169 and wall 165, allowing air to flow through, such as inlet air that may be blown by a fan 202, for example. The baffle 169 can encourage mixing of the air within the odor chamber and promotes movement of odor particles into the odor presentation tube. In various embodiments, an odor source such as may be contained in an odor source material is placed in chamber 171, and a fan 202 is attached to the outer wall 165 in chamber 172. This arrangement facilitates the desired fluid flow during operation.

A valve housing 180 is securable to the platform 152 adjacent the trays 164. The valve housing 180 includes a first end 182 having slots 185, 186 for receiving valves 191, 192 and a second end 184 with a gear drive head 222 for driving valve 191. The bottom surface 181 of the valve housing 180 is formed with air inlet openings 187, 188 for permitting access to outside air which may be drawn in by fan 202 during operation, for example. The top surface (not shown) of the valve housing 180 is similarly provided with odor outlet slots (not shown) that align with slots 199 in the platform 152 so as to permit desired odors to travel from the odor trays 164 through the slots 199 and out the odor channel 197 of the odor presentation port tube 158. The air inlet openings 187, 188 on the bottom surface 181 are adjacent the first end 182 of the valve housing 180 whereas the odor outlet slots are adjacent the second end 184 of the valve housing 180. The air inlet openings 187, 188 are not directly below the odor outlet openings as such an arrangement would not permit the desired fluid travel during operation. Removable covers 170 are also provided for closing the chambers 171, 172 of the trays 164 for operation.

Figure 20:
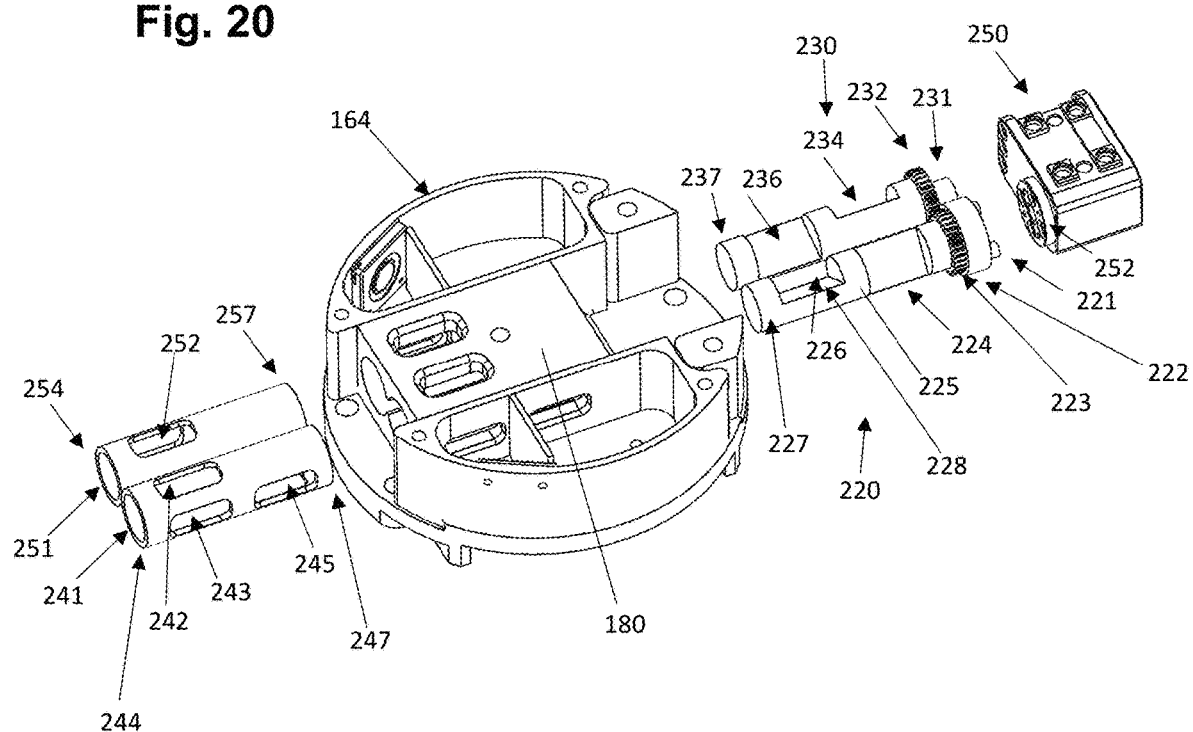
FIG. 20 is an exploded perspective view of components of the odor emitting device of FIG. 17.
Figure 21:
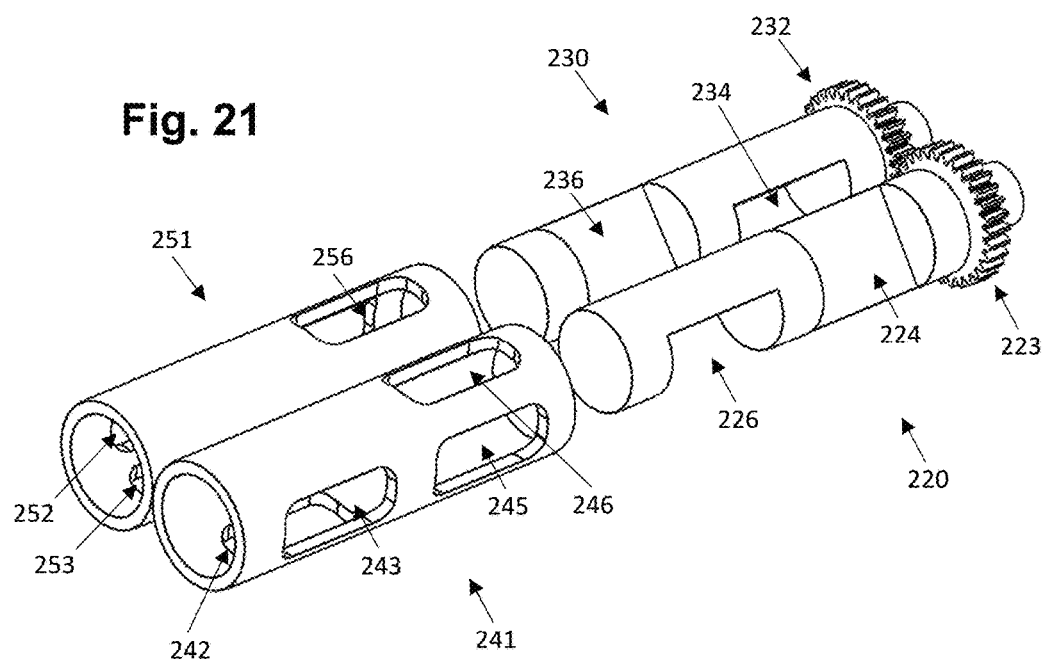
FIG. 21 is an exploded perspective view of a valve arrangement in accordance with embodiments of the present disclosure.

In various embodiments, the valves 191, 192 can be formed as valve cylinders 220, 230 that fit within valve sleeves 241, 251, respectively. The paired valve cylinders 220, 230 are substantially cylindrical and can be formed as mirror images of one another so as to facilitate fluid flow of air and odors through different compartments depending upon intended operation of the device 12. As shown in FIG. 20, for example, the valve cylinders include a drive cylinder 220 and an output cylinder 230. The drive cylinder 220 and output cylinder 230 are initially set up in a cooperative relationship so as to facilitate setting the valve in fully open, partially open, closed and flush settings, as desired during operation. For example, the drive cylinder 220 has a first end 221 with a head 222 adapted to mate with a drive 252 of an actuator 250. The head 222 has a drive gear 223 secured thereto. A first fluid slot 224 is formed in the body 225 of the drive cylinder 220 near the first end 221 as shown in FIG. 20. A second fluid slot 226 is formed in the body 225 of the drive cylinder 220 near a second end 227, as shown in FIG. 20. The slots 224, 226 can be formed as a semi-cylindrical gap, for example. In various embodiments, the slots 224, 226 are unaligned in that the edge 228 of the slot 226 would bisect the slot 224 if the edge 228 were extended through the slot 224 to the first end 221 of the drive cylinder 220. The second fluid slot 226 can be considered an air inlet slot and the first fluid slot 224 can be considered an odor outlet slot.

The output cylinder 230 can be formed similarly to drive cylinder 220, except that instead of having a head with a drive gear 223, the output cylinder 230 has a head at the first end 231 with an output gear 232. Further, while the output cylinder can be formed with a first fluid slot 234 near the first end 231 and a second fluid slot 236 near the second end 237, and while the slots 234, 236 can be formed as unaligned semi-cylindrical gaps, the orientation of the slots 234, 236 is different from the orientation of slots 224, 226 in the drive cylinder 220. The second fluid slot 236 can be considered an air inlet slot and the first fluid slot 234 can be considered an odor outlet slot. As shown in FIGS. 20 through 27, the first slot 224 of drive cylinder 220 is approximately ¼ turn counterclockwise from the first slot 234 of output cylinder 230. Further the second slot 226 of drive cylinder 220 is approximately ¼ turn clockwise from the second slot 236 of output cylinder 230. This arrangement assists with the desired fluid flow provided by the device 12. Depending upon the rotation, the slots 224, 226 in the drive cylinder 220 can be mirror images of the slots 234, 236 in the output cylinder 230.

The valve sleeves 212 are substantially cylindrical and include a valve sleeve 241 for the drive cylinder 220 and a valve sleeve 251 for the output cylinder 230. In various embodiments, the valve sleeves 241, 251 are mirror images of each other. Valve sleeve 241 includes a pair of air inlet slots 242, 243 at a first end 244 adjacent the air flow, and a pair of odor outlet slots 245, 246 adjacent a second end 247 nearest the drive gear 223 when installed. Slots 242, 243 are approximately ¼ circumferential travel apart, slots 245, 246 are approximately ¼ circumferential travel apart and slots 243, 245 are axially aligned. Similarly, valve sleeve 251 includes a pair of air inlet slots 252, 253 at a first end 254 adjacent the air flow, and a pair of odor outlet of slots 255, 256 adjacent a second end 257 nearest the output gear 232 when installed. Slots 252, 253 are approximately ¼ circumferential travel apart, slots 255, 256 are approximately ¼ circumferential travel apart and slots 253, 255 are axially aligned.

As can be seen in FIG. 20, the gear arrangement 223, 232 is secured between the actuator 250 and the valves 220, 230. The actuator 250 can be secured to the platform 152 by screws or the like. When the valve cylinders 220, 230 are installed together with corresponding valve sleeves 241, 251, respectively, the valve cylinders 220, 230 of the assembled valves 190 are rotatable by the actuator 250 and gear arrangement 223, 232 so as to position the slot 226 of the drive cylinder 220 in and out of alignment with air inlet slots 242, 243 on valve sleeve 241, and further to position the slot 236 of output cylinder 230 into and out of alignment with air inlet slots 252, 253 on valve sleeve 251. At the same time, rotation of the gear arrangement 223, 232 by the actuator rotates the slot 224 of the drive cylinder 220 into and out of alignment with the odor outlet slots 245, 246 on valve sleeve 241, and further rotates the slot 234 of the output cylinder 230 into and out of alignment with the odor outlet slots 255, 256 on valve sleeve 251. It will be appreciated that the sleeves 241, 251 are maintained in a fixed position within the valve housing 180. According to the above operation, the valves can rotate between a full fluid communication position with the odor trays 164 and a blocked fluid communication position with the odor trays, with an infinite number of intermediate positions available to permit partial fluid communication.

Due to the coordination of the various slots, it will be appreciated that the device 12 can operate such that the valve cylinders 220, 230 are rotatable such that one odor tray is in full fluid communication with the odor presentation port tube 158 while the other odor tray is fully blocked from the odor presentation port tube 158. In other embodiments, the device 12 can be operated such that both odor trays are in partial fluid communication with the odor presentation port tube.

Figure 22:
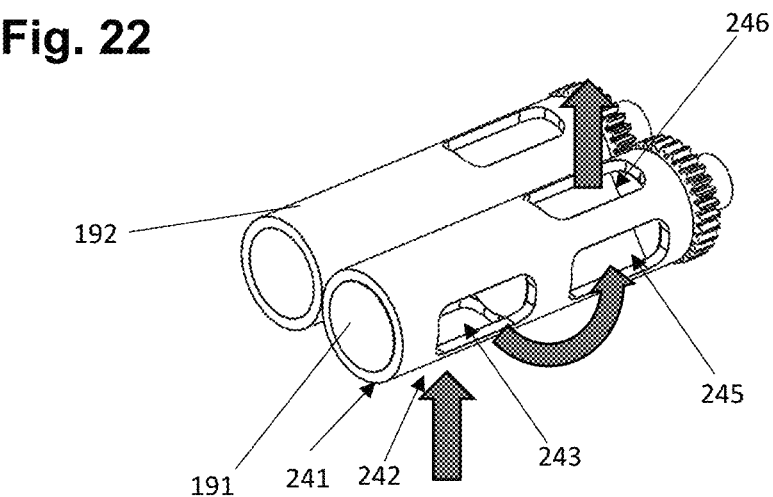
FIG. 22 is a perspective view illustrating valve operation of the valve arrangement of FIG. 21.
Figure 23:
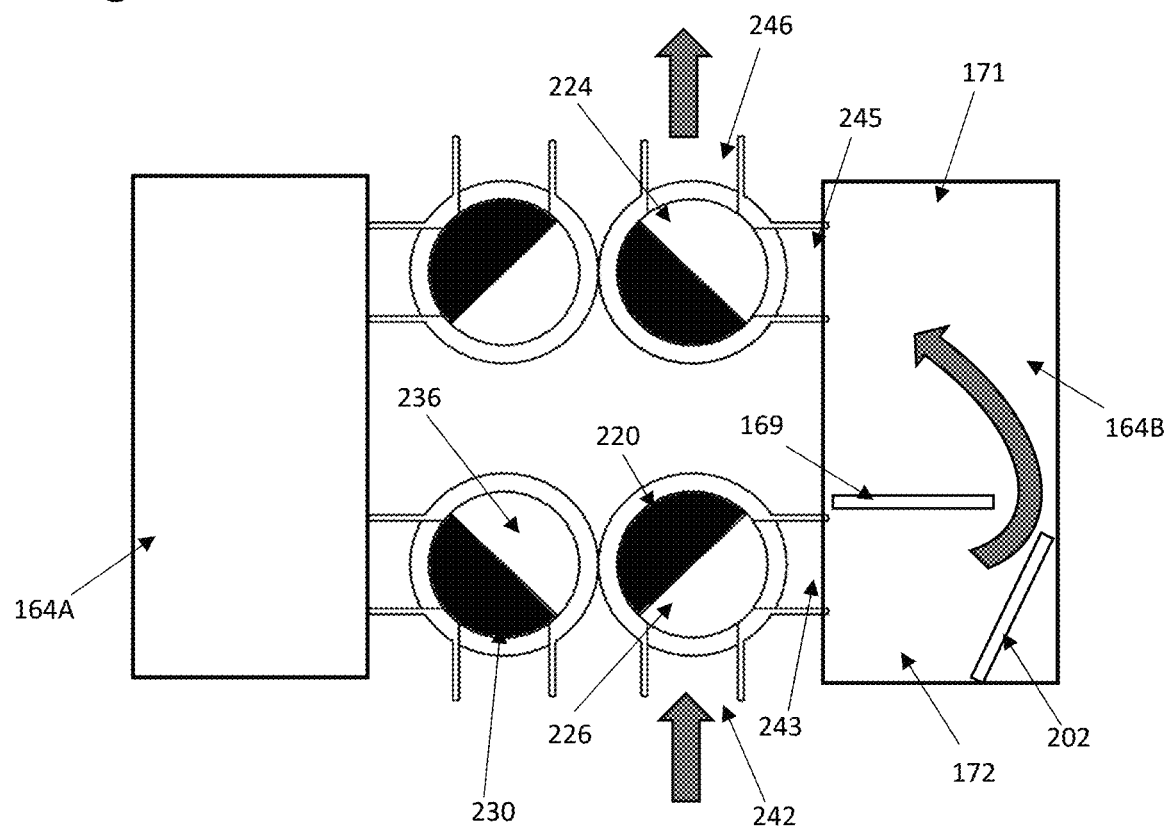
FIG. 23 is a schematic diagram illustrating valve operation of the valve arrangement of FIG. 21.
Figure 24:
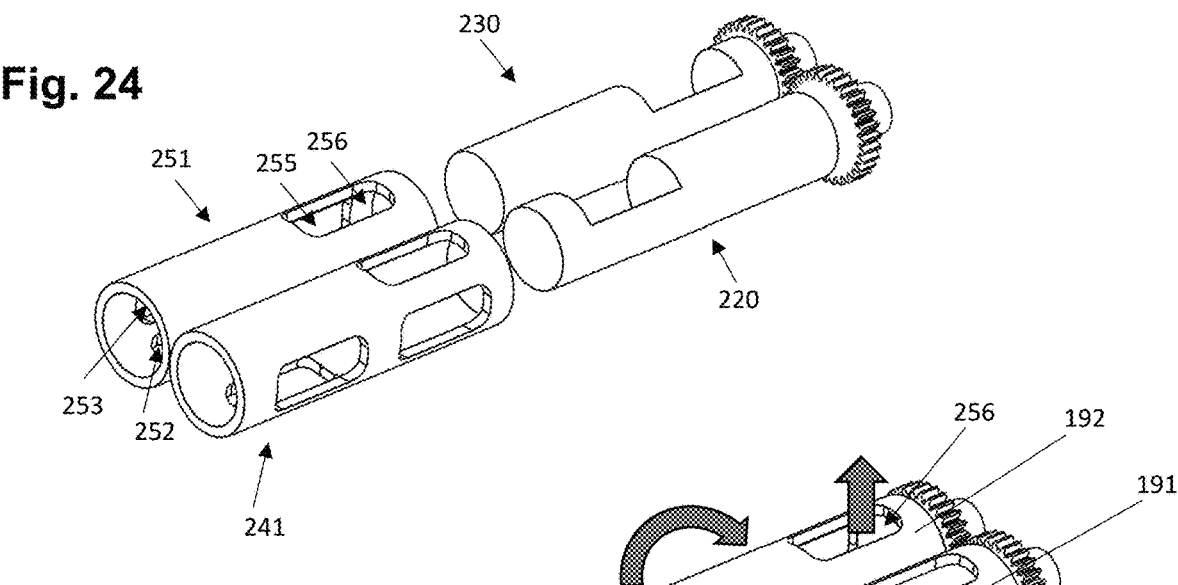
FIG. 24 is an exploded perspective view of a valve arrangement in accordance with additional embodiments of the present disclosure.

FIGS. 22 and 23 illustrate operation of valve 191 with drive cylinder 220 and valve 192 with output cylinder 230 when a left-side odor tray 164A (and any odor source material contained therein) is sealed or blocked from communication with air inlets and with the odor presentation port tube while a right-side odor tray 164B is open and permits fluid flow. FIGS. 22 and 23 correspond to the exploded arrangement shown in FIG. 21. In this environment, it will be appreciated that the fan (not shown) associated with left-side odor tray 164A may be inactive while the fan 202 associated with right-side odor tray 164B is active and facilitating air and odor flow. In operation, fresh air can flow in air inlet slot 242 of sleeve 241 and through air inlet slot 243 of sleeve 241. In doing so, the air flows through the gap or slot 226 of the drive valve cylinder 220 and into air chamber 172 of the odor tray 164B. The fan 202 assists in driving the fresh air around the baffle 169 where it is mixed with the odor source material in tray 164B and flows out of the odor outlet slots 245, 246 of the sleeve 241. It will be appreciated that air can also flow via natural convection without the assistance of a fan. In doing so, the odor flows through the gap or slot 224 of the drive valve cylinder 220 and out to the odor presentation port tube 158.

Figure 25:
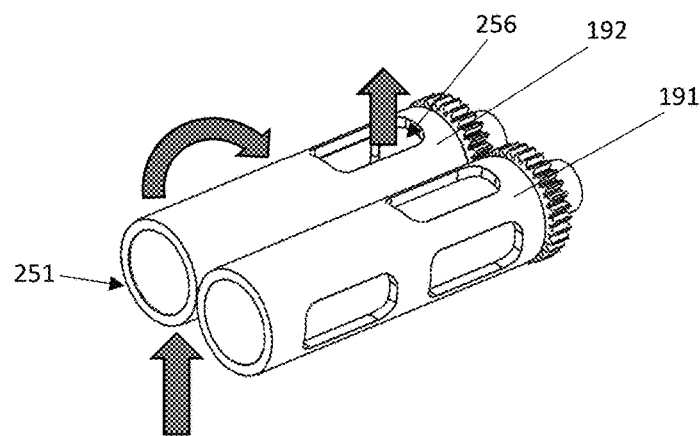
FIG. 25 is a perspective view illustrating valve operation of the valve arrangement of FIG. 24 in assembled form.
Figure 26:
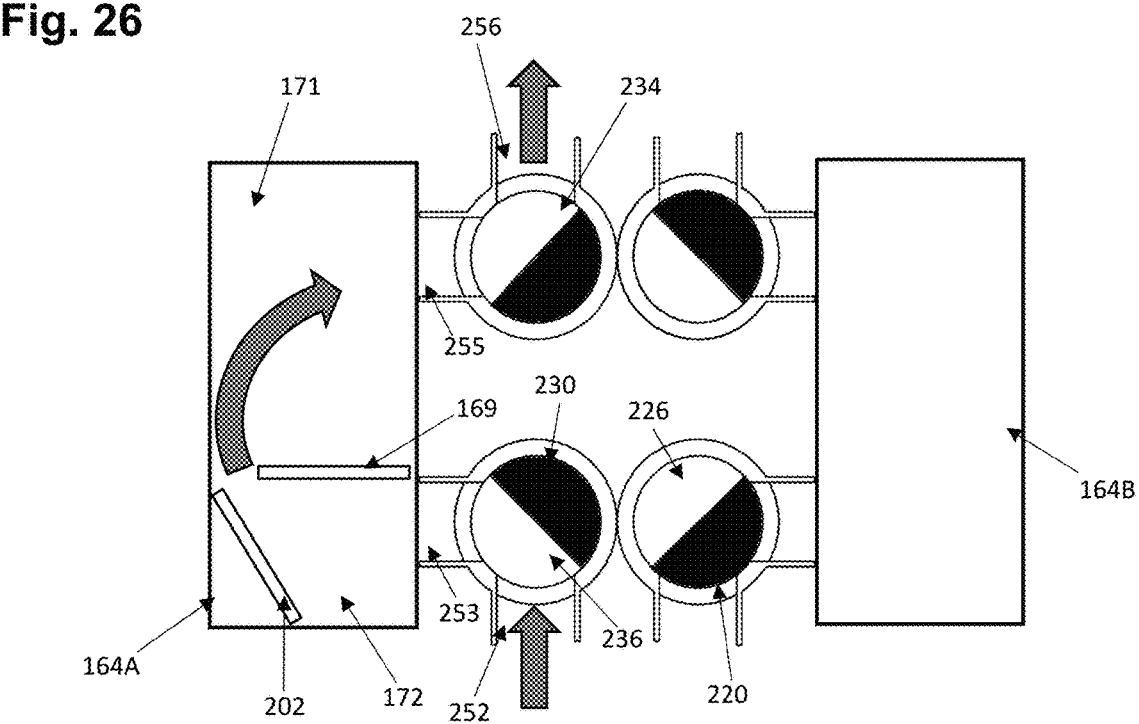
FIG. 26 is a schematic diagram illustrating valve operation of the valve arrangement of FIG. 24.

FIGS. 25 and 26 illustrate operation of valve 191 with drive cylinder 220 and valve 192 with output cylinder 230 when a right-side odor tray 164B (and any odor source material contained therein) is sealed or blocked from communication with air inlets and with the odor presentation port tube while a right-side odor tray 164A is open and permits fluid flow. FIGS. 25 and 26 correspond to the exploded arrangement shown in FIG. 24. In this environment, it will be appreciated that the fan associated with right-side odor tray 164B may be inactive while the fan 202 associated with left-side odor tray 164A is active and facilitating air and odor flow. In operation, fresh air can flow in air inlet slot 252 of sleeve 251 and through air inlet slot 253 of sleeve 251. In doing so, the air flows through the gap or slot 236 of the output valve cylinder 230 and into air chamber 172 of the odor tray 164A. The fan 202 assists in driving the fresh air around the baffle 169 where it is mixed with the odor source material in tray 164A and flows out of the odor outlet slots 255, 256 of the sleeve 251. In doing so, the odor flows through the gap or slot 234 of the drive valve cylinder 230 and out to the odor presentation port tube 158.

As shown in FIG. 23, the odor outlet slot 226 of the valve cylinder 220 is in full fluid communication position with tray 164B when the odor outlet slot 236 of valve cylinder 230 is in a blocked fluid communication position with tray 164A. However, as shown in FIG. 26, the odor outlet slot 226 of the valve cylinder 220 is in a blocked fluid communication position with tray 164B when the odor outlet slot 236 of valve cylinder 230 is in a full fluid communication position with tray 164A.

It will be appreciated that the two-odor device 12 can be operated such that the odor trays are both partially open so as to permit a blend of odors from source materials in respective odor trays (e.g., trays 164A and 164B in FIGS. 23 and 26). The position is infinitely variable to allow partial opening of the valve. Since the concentration of odor in an airflow of constant rate is proportional to the area of the valve exposed to the odor-containing air, the system as disclosed herein can therefore vary the concentration of odor in the exiting air by changing the angular position of the valve. The fan speed can also be varied for additional control.

The actuator 250 and the fan(s) 202 can be operable using at least one battery 215 and at least one controller 208 secured to the device 12. The controller 208 can receive instructions from central control unit 20 regarding a desired odor flow and the fan(s) 202 and/or actuator 250 are operated accordingly. It will further be appreciated that the odor presentation port tube 158 can be changed in size to accommodate varying sizes of animals. Also, the same fan(s) 202, or alternatively, a larger separate fan, provides the ability to flush the odor(s) from the odor presentation port tube 158. In various embodiments, a resistive electric heating element 198 is in contact with or proximate the odor presentation port tube 158 and can be energized via controller 120 to heat the surface of the tube 158 to further promote the release of adsorbed odor molecules.

It will be appreciated that embodiments of the present disclosure permit target odors to be presented to animals over a wide range of concentrations. This presents the operator with the ability to imprint odors on animals at a higher, more easily detected concentration and also to evaluate the animals' abilities to detect lower concentrations using the same system. The high repeatability of the device also enables use in cross-validation studies where animals are compared to one another.

In the embodiments described above for device 14 with four trays, target odors (e.g., TNT) may be mixed with other distractor odors in known amounts and presented to an animal for discrimination. In the embodiments described above for device 12 with two trays, either the target odor or a control odor may be presented. The actuator can move the valve drive cylinder 220 to either allow airflow across an odor sample housed in a tray or seal it from the ambient air flow when not in use. Regardless of form, the device minimizes leakage and cross-contamination of odors. By permitting the valve to be positioned to allow a varying area of the odor source material to be exposed, the device permits proportional control of the odor's concentration in the produced odor plume. The fan ensures a positive air flow across the sample, the speed of which can be varied as well. Odors can be quickly and easily changed by removing the trays 64, 164. Odor concentrations can be varied over time by the central control unit 20, for example, producing "pulses" if desired, or dynamically varying concentrations to increase difficulty for animals.

In various embodiments, the odor path components are coated in a silicon-based material that lowers surface energy and discourages adsorption of odor molecules. The odor canister devices 12, 14 can further be produced such that any surface that contacts an odor is made of metal and can easily be isolated from any plastic parts. This allows the odor path components to be baked in an oven to thoroughly clean them via evaporation, either as part of periodic maintenance or when changing odors, for example.

Through operation of the device 12 and/or 14 as described herein, a suitable quantity and concentration of a desired vapor (e.g., TNT) is released and cutoff as desired. When not in use, there is no detectable leakage of the vapor to the ambient environment. Further, surfaces within and surrounding the device do not accumulate or adsorb odor. The devices have no unintended cues that signal the production of a target odor (versus control or distractor), other than the odor itself.

With further reference to FIG. 1, a reward dispenser 16 according to the present disclosure can be provided as a type of vibratory pellet feeder that may be suitable for rewarding small animals, a gel dispenser to provide a syrup or semi-solid reward or a compressed air cartridge and valve to launch a playing item such as a tennis ball as part of a play reward for dogs. Various sizes of pellets can be used after modification of the vibratory dispensing mechanism. In various embodiments, the reward dispenser 16 includes an embedded microcontroller similar to microcontrollers 208, 120 of devices 12, 14, respectively. The reward-emitting device 16 can thus include a reward-emitting device microcontroller, a reward-emitting device actuator and a reward release structure. A signal light can be provided on the reward dispenser to act as a cue, for example, and the light can be triggered by microcontroller upon receiving a signal from central control unit 20 that the light should be activated. Further, an electromagnetic clicker and tone, such as an audible or an ultrasonic tone, can be emitted from the reward dispenser 16 by, for example, generating the sound by a microcontroller upon receiving a signal from central control unit 20 and emitting the sound via a loudspeaker on or in communication with the dispenser 16. In various alternative embodiments, the reward dispenser 16 is a bridge device to an existing controllable feeder or other suitable reward mechanism. For example, the bridge device can include a microcontroller and a radio transmitter for sending signals to an existing reward mechanism. As a specific example, the bridge device can receive signals from the central control unit 20 as described elsewhere herein, and when such signals indicate that a reward is to be provided, the bridge device can send a signal to close switch contacts on an existing canine treat dispenser.

The embedded microcontroller on the odor canister devices 12, 14 and reward dispenser(s) 16 coordinates all functions of the respective devices, including control of actuators, control of fans, control of lights, control of heating elements, acquisition of sensor data (e.g., odor tray present sensor or head poke sensor), monitoring of system function and health (verifying correct sensor and actuator function), battery voltage monitoring, usage statistics, and data transmission and receipt from the communications component 24. In various embodiments, the actuators 90, 250 may contain an internal or external position encoder that measures the angular position of the valve. Inside the microcontroller firmware, this information is compared to the desired position and a fault is issued and reported to the central control unit 20 if the positions do not match within a specified tolerance. When present, this condition indicates a mechanical problem.

It will be appreciated that odor canister devices 12, 14 and reward dispenser 16 can be housed in high-impact enclosures made of suitable polymers. A wireless radio module (e.g., wi-fi or Zigbee or equivalent protocol) can be provided with the embedded microcontroller to establish bidirectional communication between the devices and the system base station. The radio modules can connect to the microcontroller via a serial port, for example.

Software programming in accordance with the present disclosure allows definition of animal performance metrics that are defined from available event data and animal position. For example, the time required to locate TNT is the elapsed time between the TNT valve being opened and the animal holding its head in the correct port for a specified time. These metrics can be collected by performance metric component 27 and stored in database 40 that can be queried for any type of comparison or analysis. It is desirable in many cases to identify animals that are not likely to succeed at the training at an early time, so they can be removed from training before resources are wasted. In various embodiments, the prediction component 28 of the present system contains a machine learning algorithm that uses early stage training data to form mathematical models that assess an animal's likelihood of underperforming in the final odor search test.

The system software can include a graphical application, supporting touch screen functionality in various embodiments. The fully configurable software performs all operations relating to system function, including logic flow, acquisition of sensor data such as nose pokes, faults, etc., issuance of actuation commands such as valve opening, tone on/off, etc., logging of events and faults, and full analysis of trends from previous sessions. Such trends can include animal performance characteristics over time, and comparison between animals, for example.

Figure 27:
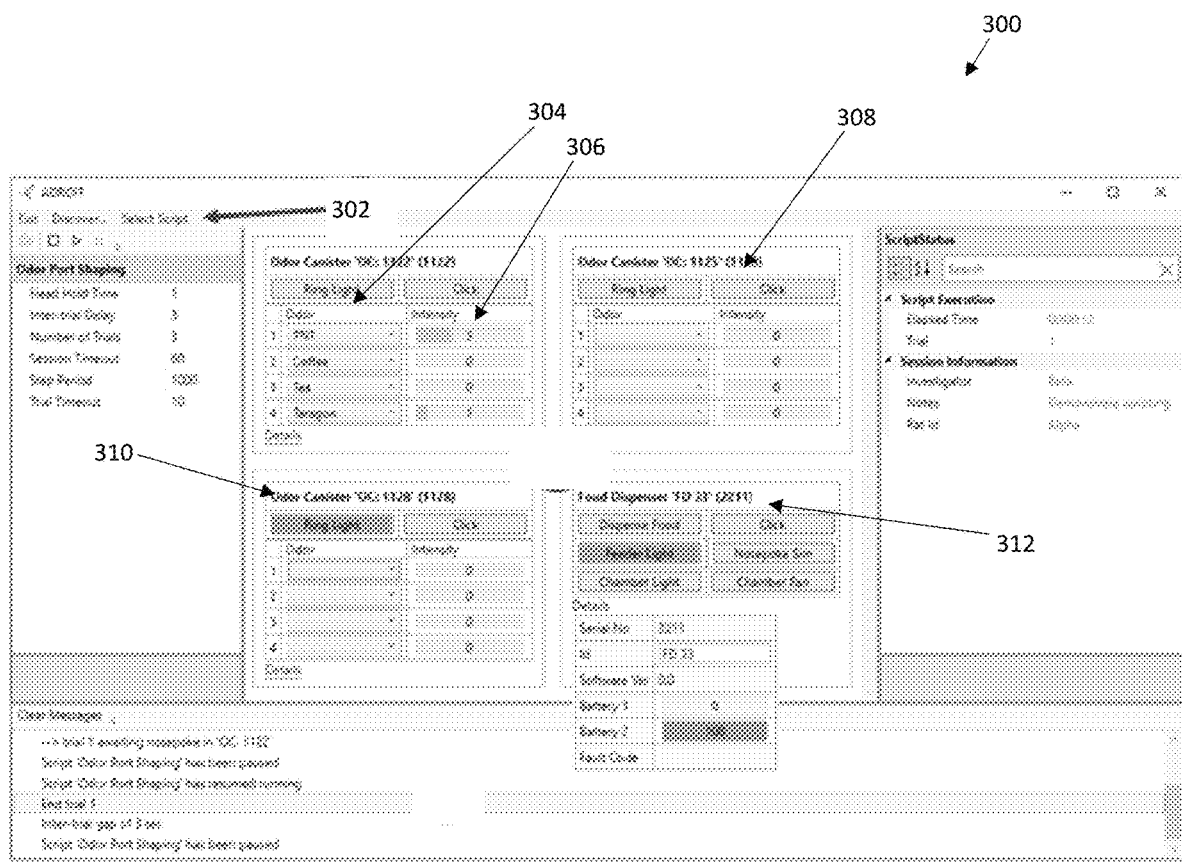
FIG. 27 is an exemplary screen shot of a user interface in accordance with embodiments of the present disclosure.

FIG. 27 illustrates a sample user interface 300 that can be employed with software programming associated with the present system. As seen in FIG. 27, the user can build and select scripts as at 302 for directing operation of one or more of the devices 12, 14, 16. The interface 300 can reveal as at 304 what odors are present in the trays of an odor-emitting device 14, and can reveal as at 306 the intensity of the odor emission based on the settings of the valves. Details of additional odor-emitting device settings are shown at 308 and 310, and details of reward-emitting device settings are shown at 312.

As will be appreciated from the present disclosure, embodiments of a system can include at least one odor-emitting device, at least one reward-emitting device and a central control unit or base station in communication with the odor-emitting device and the reward-emitting device. The odor-emitting device can include a housing defining an odor channel, at least one odor tray secured within the housing, a controller secured within the housing, a valve actuator secured within the housing, a valve secured within the housing and a head detector secured within the housing. The reward-emitting device can include a reward-emitting device controller, a reward-emitting device actuator and a reward release structure. The central control unit can include a processor and a memory storing instructions that, when executed by the processor, cause the processor to receive an instruction to move the valve of the at least one odor-emitting device, communicate a first signal to the odor-emitting device controller to trigger the valve actuator to move the valve, receive a signal from the odor-emitting device controller that the first head detector has detected a head movement or a head position placement of an animal; and communicate a first signal to the reward-emitting device controller to trigger the reward-emitting device actuator to open the reward release structure, whereby a reward stored in the reward release structure can be released.

In embodiments, the first signal to the odor-emitting device controller triggers the valve actuator to move the valve to an open position whereby the at least one odor tray is in fluid communication with the odor channel. The processor can also communicate a second signal to the odor-emitting device controller to trigger the valve actuator to move the valve. It will be appreciated that the second signal to the odor-emitting device controller can trigger the valve actuator to move the valve to a closed position whereby the at least one odor tray is closed to fluid communication with the odor channel. The valves can be moved to mix odors or emit odors from multiple odor devices.

In various embodiments, the processor can, via prediction component 28, predict the animal's likelihood of meeting a performance metric based at least upon the elapsed time period.

The above-described embodiments of the present disclosure may be implemented in accordance with or in conjunction with one or more of a variety of different types of systems, such as, but not limited to, those described elsewhere herein.

The present disclosure contemplates a variety of different systems each having one or more of a plurality of different features, attributes, or characteristics. A "system" as used herein can refer, for example, to various configurations of: (a) one or more odor-emitting devices; (b) one or more odor-emitting devices and one or more external computing devices such as central control unit 20; (c) one or more odor-emitting devices communicating via one or more networks; (d) one or more odor-emitting devices and one or more external computing devices communicating via one or more networks; (e) one or more personal computing devices, such as desktop computers, laptop computers, tablet computers, personal digital assistants, mobile phones, and other mobile computing devices; (f) one or more reward-emitting devices; (g) one or more odor-emitting devices and one or more reward-emitting devices; (h) one or more odor-emitting devices and one or more reward-emitting devices communicating via one or more networks; (i) one or more odor-emitting devices, one or more reward-emitting devices and one or more external computing devices; (j) one or more odor-emitting devices, one or more reward-emitting devices and one or more external computing devices communicating via one or more networks; (k) one or more sets of odor-emitting devices, one or more sets of reward-emitting devices and one or more external computing devices; (l) a base station alone or in communication with one or more of (a) through (k) above. A system as used herein can also include one or more odor-emitting and/or reward-emitting devices and a remote control unit designed to capture and amalgamate the information from connected emitting devices and transmit this information over the more general or public network with increased efficiency and security. This gateway can also act as a management tool and an emitting-device health monitor for a group of emitting devices, for example.

In certain embodiments in which the system includes a personal computing device in combination with a remote control unit, odor-emitting device or reward emitting device, the computing device is any suitable computing device (such as a server) that includes at least one processor and at least one memory device or data storage device. Further, the central control unit and the microcontrollers described herein can be any suitable computing device that includes at least one processor and at least one memory device or data storage device. As further described herein, these computing devices include at least one processor configured to transmit and receive data or signals representing events, messages, commands, or any other suitable information between the computing device and the odor-emitting device and/or reward-emitting device. The processor of the computing device is configured to execute the events, messages, or commands represented by such data or signals in conjunction with the operation of the computing device. Moreover, the microprocessor of the odor-emitting device and the reward-emitting device is configured to transmit and receive data or signals representing events, messages, commands, or any other suitable information between the respective emitting device and the computing device. The microprocessors of the odor-emitting device and reward-emitting device are configured to execute the events, messages, or commands represented by such data or signals in conjunction with the operation of such devices.

In addition, the system as presently disclosed can internally store historical data from all devices for the purposes of automatic or manual analysis to improve device operation and animal training, as well as to troubleshoot the device or the installation. Stored data can be easily retrieved over the network connection or by physical removal of a memory device and can further be erased remotely when desired.

It will be appreciated that any combination of one or more computer readable media may be utilized. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing, including a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

As will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented as entirely hardware, entirely software (including firmware, resident software, micro-code, etc.) or combining software and hardware implementation that may all generally be referred to herein as a "circuit," "module," "component," or "system." Furthermore, aspects of the present disclosure may take the form of a computer program product embodied in one or more computer readable media having computer readable program code embodied thereon.

It will be appreciated that all of the disclosed methods and procedures herein can be implemented using one or more computer programs or components. These components may be provided as a series of computer instructions on any conventional computer-readable medium, including RAM, SATA DOM, or other storage media. The instructions may be configured to be executed by one or more processors which, when executing the series of computer instructions, performs or facilitates the performance of all or part of the disclosed methods and procedures.

Unless otherwise stated, devices or components of the present disclosure that are in communication with each other do not need to be in continuous communication with each other. Further, devices or components in communication with other devices or components can communicate directly or indirectly through one or more intermediate devices, components or other intermediaries. Further, descriptions of embodiments of the present disclosure herein wherein several devices and/or components are described as being in communication with one another does not imply that all such components are required, or that each of the disclosed components must communicate with every other component. In addition, while algorithms, process steps and/or method steps may be described in a sequential order, such approaches can be configured to work in different orders. In other words, any ordering of steps described herein does not, standing alone, dictate that the steps be performed in that order. The steps associated with methods and/or processes as described herein can be performed in any order practical. Additionally, some steps can be performed simultaneously or substantially simultaneously despite being described or implied as occurring non-simultaneously.

It will be appreciated that algorithms, method steps and process steps described herein can be implemented by appropriately programmed computers and computing devices, for example. In this regard, a processor (e.g., a microprocessor or controller device) receives instructions from a memory or like storage device that contains and/or stores the instructions, and the processor executes those instructions, thereby performing a process defined by those instructions. Furthermore, aspects of the present disclosure may take the form of a computer program product embodied in one or more computer readable media having computer readable program code embodied thereon.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on a single computer, partly on a single computer, as a stand-alone software package, partly on a device microcontroller and partly on a remote computing device or entirely on the remote computing device. Further, connection may be made to an external computer (for example, through the Internet using an Internet Service Provider) or in a cloud computing environment or offered as a service such as a Software as a Service (SaaS). It will be appreciated that the computer code may also be implemented using an RTOS (real time operating system) together with appropriate application code to provide a faster response capability.

Where databases are described in the present disclosure, it will be appreciated that alternative database structures to those described, as well as other memory structures besides databases may be readily employed. The drawing figure representations and accompanying descriptions of any exemplary databases presented herein are illustrative and not restrictive arrangements for stored representations of data. Further, any exemplary entries of tables, charts, graphs and parameter data represent example information only, and, despite any depiction of the databases as tables, other formats (including relational databases, object-based models and/or distributed databases) can be used to store, process and otherwise manipulate the data types described herein. Electronic storage can be local or remote storage, as will be understood to those skilled in the art. Appropriate encryption and other security methodologies can also be employed by the system of the present disclosure, as will be understood to one of ordinary skill in the art.

The invention claimed is:

1. An odor-emitting device, comprising:
a platform;
a tube receiver maintained atop the platform, wherein the tube receiver comprises a rim forming a rim opening therein;
an odor presentation port tube positioned within the rim opening of the tube receiver, wherein the odor presentation port tube comprises a wall formed with an odor channel therein;
first and second trays removably securable to the platform;
a valve housing securable to the platform adjacent the first and second trays;
a valve secured within the valve housing;
an actuator secured to the platform and adapted to move the valve; and
a gear arrangement secured between the actuator and the valve; wherein the valve comprises first and second valve sleeves, wherein the first valve sleeve houses a first valve cylinder formed with a first pair of fluid slots, wherein the first pair of fluid slots are formed as gaps in an outer surface of the first valve cylinder, wherein the first valve cylinder is rotatable by the actuator and gear arrangement so as to selectively position a first one or both of the first pair of fluid slots at a position in between a full fluid communication position with the first tray and a blocked fluid communication position with the first tray, and
wherein the second valve sleeve houses a second valve cylinder formed with a second pair of fluid slots, wherein the second pair of fluid slots are formed as gaps in an outer surface of the second valve cylinder, and wherein the second valve cylinder is rotatable by the actuator and gear arrangement so as to selectively position a first one or both of the second pair of fluid slots at a position in between a full fluid communication position with the first tray and a blocked fluid communication position with the second tray.

2. The odor-emitting device of claim 1, wherein the gear arrangement comprises a drive gear secured to a head at a first end of the first valve cylinder and an output gear secured to a head at a first end of the second valve cylinder.

3. The odor-emitting device of claim 2, wherein the first pair of fluid slots extends in sequence axially outwardly from the drive gear along the first valve cylinder, and wherein the second pair of slots extends in sequence axially outwardly from the output gear along the second valve cylinder.

4. The odor-emitting device of claim 3, wherein the first pair of fluid slots is unaligned axially along the first valve cylinder, and wherein the second pair of fluid slots is unaligned axially along the second valve cylinder.

5. The odor-emitting device of claim 1, wherein the first valve sleeve comprises a first pair of inlet slots and a first pair of outlet slots, wherein the second valve sleeve comprises a second pair of inlet slots and a second pair of outlet slots, wherein the first pair of inlet slots are alignable with the first one of the first pair of fluid slots of the first valve cylinder, and wherein the second pair of inlet slots are alignable with the first one of the second pair of fluid slots of the second valve cylinder.

6. The odor-emitting device of claim 1, further comprising a controller operable to trigger the actuator to move the valve.

7. The odor-emitting device of claim 1, further comprising a fan securable to the valve housing.

8. The odor-emitting device of claim 7, wherein the fan and the actuator are operable by a controller secured to the device.

9. The odor-emitting device of claim 7, further comprising a controller operable to trigger the fan.

10. The odor-emitting device of claim 7, wherein the fan is a variable speed fan.

11. The odor-emitting device of claim 7, wherein the fan comprises a first fan secured to the first tray and a second fan secured to the second tray.

12. The odor-emitting device of claim 1, further comprising a first odor within the first tray and a second odor within the second tray, wherein the actuator is operable by a controller to independently control mixing of the first odor with air, the first odor with the second odor and the second odor with air.

\* \* \* \* \*